US009233164B2

(12) United States Patent
Kabanov et al.

(10) Patent No.: US 9,233,164 B2

(45) Date of Patent: Jan. 12, 2016

(54) WATER SOLUBLE FULLERENE FORMULATIONS AND METHODS OF USE THEREOF

(75) Inventors: Alexander V. Kabanov, Chapel Hill, NC (US); Jing Tong, Omaha, NE (US)

(73) Assignee: BOARD OF REGENTS OF THE UNIVERSITY OF NEBRASKA, Omaha, NE (US)

(*) Notice: Subject to any disclaimer, the term of this patent is extended or adjusted under 35 U.S.C. 154(b) by 0 days.

(21) Appl. No.: 13/976,245

(22) PCT Filed: Jan. 13, 2012

(86) PCT No.: PCT/US2012/021234

§ 371 (c)(1), (2), (4) Date: Aug. 9, 2013

(87) PCT Pub. No.: WO2012/097245

PCT Pub. Date: Jul. 19, 2012

(65) Prior Publication Data

US 2013/0323188 A1 Dec. 5, 2013

Related U.S. Application Data

(60) Provisional application No. 61/432,639, filed on Jan. 14, 2011.

(51) Int. Cl.

| | |
|---|---|
| ***A61K 47/48*** | (2006.01) |
| ***A61Q 17/04*** | (2006.01) |
| ***A61Q 1/02*** | (2006.01) |
| ***A61Q 19/00*** | (2006.01) |
| ***A61Q 19/06*** | (2006.01) |
| ***A61Q 13/00*** | (2006.01) |
| ***A61K 8/81*** | (2006.01) |
| ***A61Q 19/08*** | (2006.01) |
| ***A61K 8/84*** | (2006.01) |
| ***A61K 9/51*** | (2006.01) |
| ***A61K 31/015*** | (2006.01) |
| ***C08G 73/02*** | (2006.01) |
| ***C08L 79/02*** | (2006.01) |
| ***A61K 8/19*** | (2006.01) |

(52) U.S. Cl.

CPC ............. *A61K 47/48176* (2013.01); *A61K 8/19* (2013.01); *A61K 8/817* (2013.01); *A61K 8/84* (2013.01); *A61K 9/5138* (2013.01); *A61K 31/015* (2013.01); *A61Q 1/02* (2013.01); *A61Q 13/00* (2013.01); *A61Q 17/04* (2013.01); *A61Q 19/00* (2013.01); *A61Q 19/007* (2013.01); *A61Q 19/06* (2013.01); *A61Q 19/08* (2013.01); *C08G 73/0233* (2013.01); *C08L 79/02* (2013.01); *A61K 2800/10* (2013.01); *A61K 2800/522* (2013.01)

(58) Field of Classification Search

None

See application file for complete search history.

(56) References Cited

U.S. PATENT DOCUMENTS

| | | | | |
|---|---|---|---|---|
| 5,281,653 | A * | 1/1994 | Thomann et al. | 524/490 |
| 7,186,274 | B2 | 3/2007 | Vic et al. | |
| 2007/0298006 | A1 | 12/2007 | Tomalia et al. | |
| 2009/0012033 | A1 | 1/2009 | DeMattei et al. | |
| 2009/0238779 | A1 * | 9/2009 | Jensen et al. | 424/53 |
| 2010/0028559 | A1 | 2/2010 | Yan et al. | |
| 2010/0069536 | A1 * | 3/2010 | Sau | 524/48 |

FOREIGN PATENT DOCUMENTS

| | | |
|---|---|---|
| WO | 2011/127256 | 10/2011 |

OTHER PUBLICATIONS

Zheng et al. "Synthesis and Identification of Heterocyclic Derivatives of Fullerene C60: Unexpected Reaction of Anionic C60 with Benzonitrile".J Org. Chem. 2008, 73, 3159-3168.*

Tokuyama et al. "Photoinduced Biochemical Activity of Fullerene Carbocyclic Acid" J. Am. Chem. Soc. 1993, 115, 7918-7919.*

Gaertner, F.C., et al. "Synthesis, biodistribution and excretion of radiolabeled poly(2-alkyl-2-oxazoline)s." J Control Release. Jun. 22, 2007;119(3):291-300. Epub Mar. 2, 2007.

Tong, J., et al. "Protein modification with amphiphilic block copoly(2-oxazoline)s as a new platform for enhanced cellular delivery." Mol Pharm. Aug. 2, 2010;7(4):984-92.

Xiao, L., et al. "Antioxidant effects of water-soluble fullerene derivatives against ultraviolet ray or peroxylipid through their action of scavenging the reactive oxygen species in human skin keratinocytes." Biomed Pharmacother. Aug. 2005;59(7):351-8.

Luxenhofer, R., et al. "Doubly amphiphilic poly(2-oxazoline)s as high-capacity delivery systems for hydrophobic drugs." Biomaterials. Jun. 2010;31(18):4972-9. Epub Mar. 26, 2010.

Ungurenasu, C., et al. "Highly stable C(60)/poly(vinylpyrrolidone) charge-transfer complexes afford new predictions for biological applications of underivatized fullerenes." J Med Chem. Aug. 10, 2000;43(16):3186-8.

Hoogenboom, R. "Poly(2-oxazoline)s: a polymer class with numerous potential applications." Angew Chem Int Ed Engl. 2009;48(43):7978-94.

Tokuyama, et al. "Photoinduced biochemical activity of fullerene carboxylic acid." Journal of America Chemical Society. 1993;115(17):7918-7919.

* cited by examiner

*Primary Examiner* — Robert A Wax

*Assistant Examiner* — Danah Al-Awadi

(74) *Attorney, Agent, or Firm* — Robert C. Netter, Jr.; Dann, Dorfman, Herrell & Skillman

(57) ABSTRACT

The present invention provides water soluble fullerene formulations and methods of use thereof.

17 Claims, 18 Drawing Sheets

WATER SOLUBLE FULLERENE FORMULATIONS AND METHODS OF USE THEREOF

Figure 1:
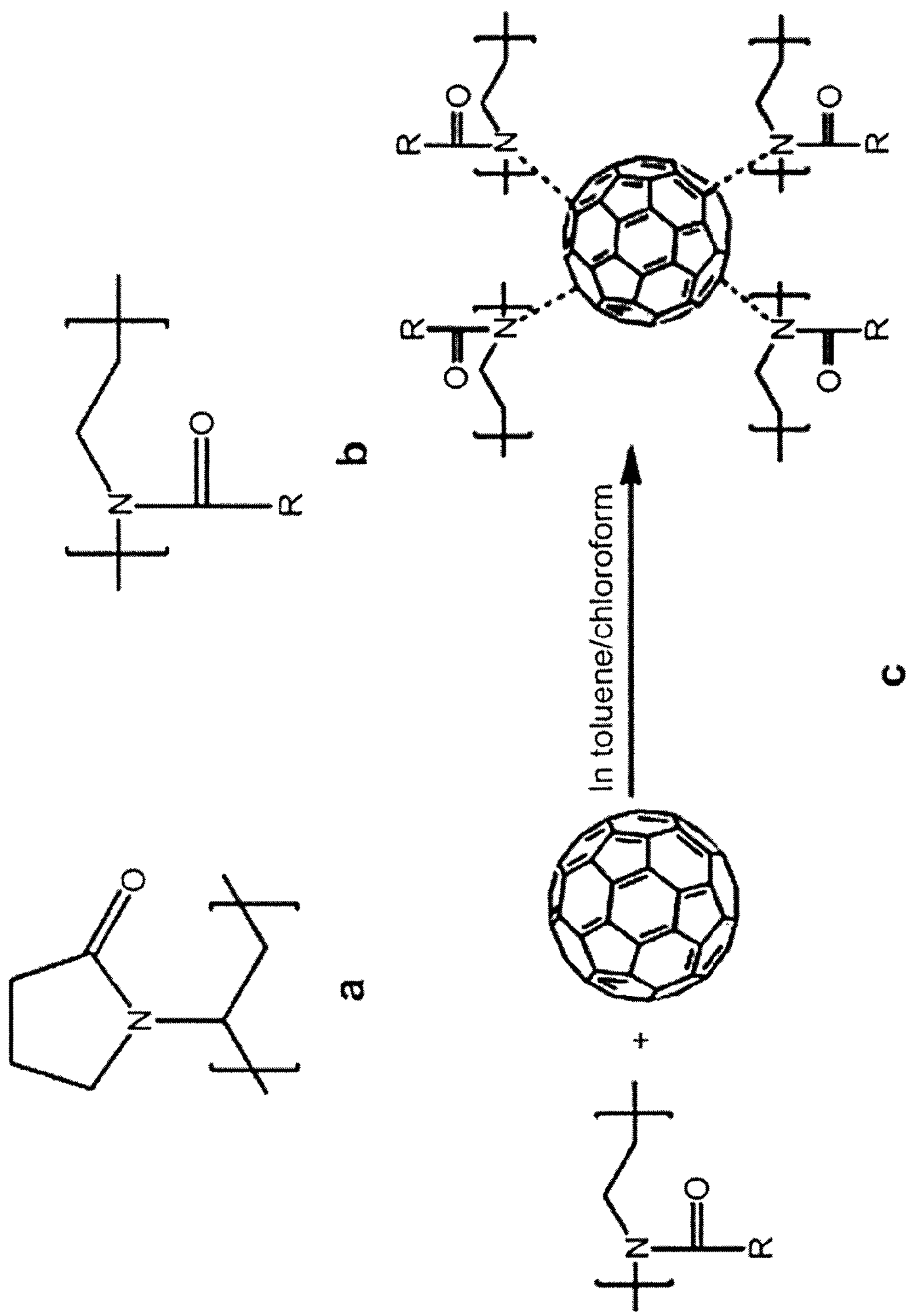

This application is a §371 application of PCT/US2012/021234, filed Jan. 13, 2012, which claims priority under 35 U.S.C. §119(e) to U.S. Provisional Patent Application No. 61/432,639, filed Jan. 14, 2011. The foregoing applications are incorporated by reference herein.

This invention was made with government support under Grant No. RR021937 awarded by the National Institutes of Health. The government has certain rights in the invention.

FIELD OF THE INVENTION

The present invention relates generally to the antioxidants. More specifically, the present invention relates to compositions and methods for the delivery of therapeutic antioxidants to a patient.

BACKGROUND OF THE INVENTION

The unique physical and chemical properties of fullerene (e.g., $C_{60}$) have elicited broad research interest from different areas since it was discovered in 1985 (Kroto et al. (1985) Nature 318:162-3; Kroto et al. (1991) Chem. Rev., 91:1213-35). Over the past 20 years, fullerene has been investigated as a radical scavenger, due to its highly unsaturated structure and excellent electron-receptor properties (Bosi et al. (2003) Eur. J. Med. Chem., 38:913-23; Krusic et al. (1991) Science 254: 1183-5; McEwen et al. (1992) J. Am. Chem. Soc., 114:4412-4; Markovic et al. (2008) Biomaterials 29:3561-73; Nakamura et al. (2003) Acc. Chem. Res., 36:807-15). It has been reported that one fullerene molecule can readily react with at least 15 benzyl radicals or 34 methyl radicals to form stable radical or non-radical adducts (Krusic et al. (1991) Science 254:1183-5). Many detrimental biological free radicals, such as superoxide ($O_2^-$), hydroxyl radical (OH), singlet oxygen ($^1O_2$) and nitrogen-based radicals can be efficiently scavenged by fullerene and fullerene derivatives (Yin et al. (2009) Biomaterials 30:611-21; Misirkic et al. (2009) Biomaterials 30:2319-28; Lin et al. (2001) Appl. Magn. Reson., 20:583-4; Dugan et al. (1997) Proc. Natl. Acad. Sci., 94:9434-9; Wang et al. (1999) J. Med. Chem., 42:4614-20). However, the extreme hydrophobicity and potential toxicity of fullerene limit its application as a therapeutic antioxidant (Nakamura et al. (2003) Acc. Chem. Res., 36:807-15). To overcome these barriers, two major categories of strategies have been developed in the last two decades: (1) synthesis of water-soluble fullerene derivatives which maintain the radical scavenging capability, such as carboxyfullerene (C3) (Dugan et al. (1997) Proc. Natl. Acad. Sci., 94:9434-9; Lamparth et al. (1994) J. Chem. Soc. Chem. Commun., 14:1727-8.) and poly-hydroxyfullerene (fullerenol) (Dugan et al. (1997) Proc. Natl. Acad. Sci., 94:9434-9; Chiang et al. (1994) J. Org. Chem., 59:3960-8); and (2) solubilization of pristine fullerene using polymer, surfactant, cyclodextrin, liposome, solvent exchange or nanomilling (Misirkic et al. (2009) Biomaterials 30:2319-28; Kato S, Kikuchi et al. (2010) J. Photochem. Photobiol. B., 98:144-51; Andrievsky et al. (1995) J. Chem. Soc. Chem. Commun., 12:1281-2; Ungurenasu et al. (2000) J. Med. Chem., 43:3186-8; Samal et al. (2000) Chem. Commun., 13:1101-2; Yamakoshi et al. (1994) J. Chem. Soc. Chem. Commun., 4:517-8; Shinohara et al. (2009) Toxicol. Lett., 191:289-96; Xiao et al. (2010) Biomaterials 31:5976-85). For example, a carboxylated fullerene derivative ($C_{60}$ tris-malonic acid) was reported to be able to protect neurons from apoptosis induced by glutamate receptor-mediated excitotoxicity, and is now being commercially developed as a therapy for neurodegenerative diseases (Dugan et al. (1997) Proc. Natl. Acad. Sci., 94:9434-9; All et al. (2008) Nanomedicine 4:283-94; Ali et al. (2004) Free Radic. Biol. Med., 37:1191-202). Several pristine fullerene formulations, such as fullerene-poly (N-vinyl pyrrolidine) (PVP) complex (Radical Sponge®) or fullerene-containing vegetable squalane (LipoFullerene®), have been approved as the antioxidant ingredients in cosmetic products and are sold in some countries (Xiao et al. (2010) Biomaterials 31:5976-85; Xiao et al. (2005) Biomed. Pharmacother., 59:3518; Xiao et al. (2006) Bioorg. Med. Chem. Lett., 16:1590-5; Lens et al. (2009) Recent Pat. Biotechnol., 3:118-23).

SUMMARY OF THE INVENTION

In accordance with the instant invention, particles comprising at least one fullerene and at least one oxazoline polymer are provided wherein the fullerene is complexed with the oxazoline polymer. Compositions comprising the particles, optionally with at least one pharmaceutically acceptable carrier or cosmetically acceptable carrier are also provided. The fullerene may be derivatized or pristine. In a particular embodiment, the fullerene is $C_{60}$ or a mixture of fullerenes comprising $C_{60}$. The oxazoline polymer may be a homopolymer or a random or block copolymer. In a particular embodiment, the oxazoline polymer comprises 2-ethyl-2-oxazoline.

In accordance with the instant invention, methods for treating, inhibiting, and/or preventing an oxidative stress associated disease or disorder in a subject are provided. The methods comprise administering to the subject at least one composition of the instant invention.

BRIEF DESCRIPTIONS OF THE DRAWING

FIG. 1A provides the structures of PVP. FIG. 1B provides the structure of POx, where R=ethyl for PEtOx and R=ethyl or butyl for P(EtOx-co-BuOx). FIG. 1C provides the proposed charge-transfer complex formation between fullerene and POx.

Figure 2:
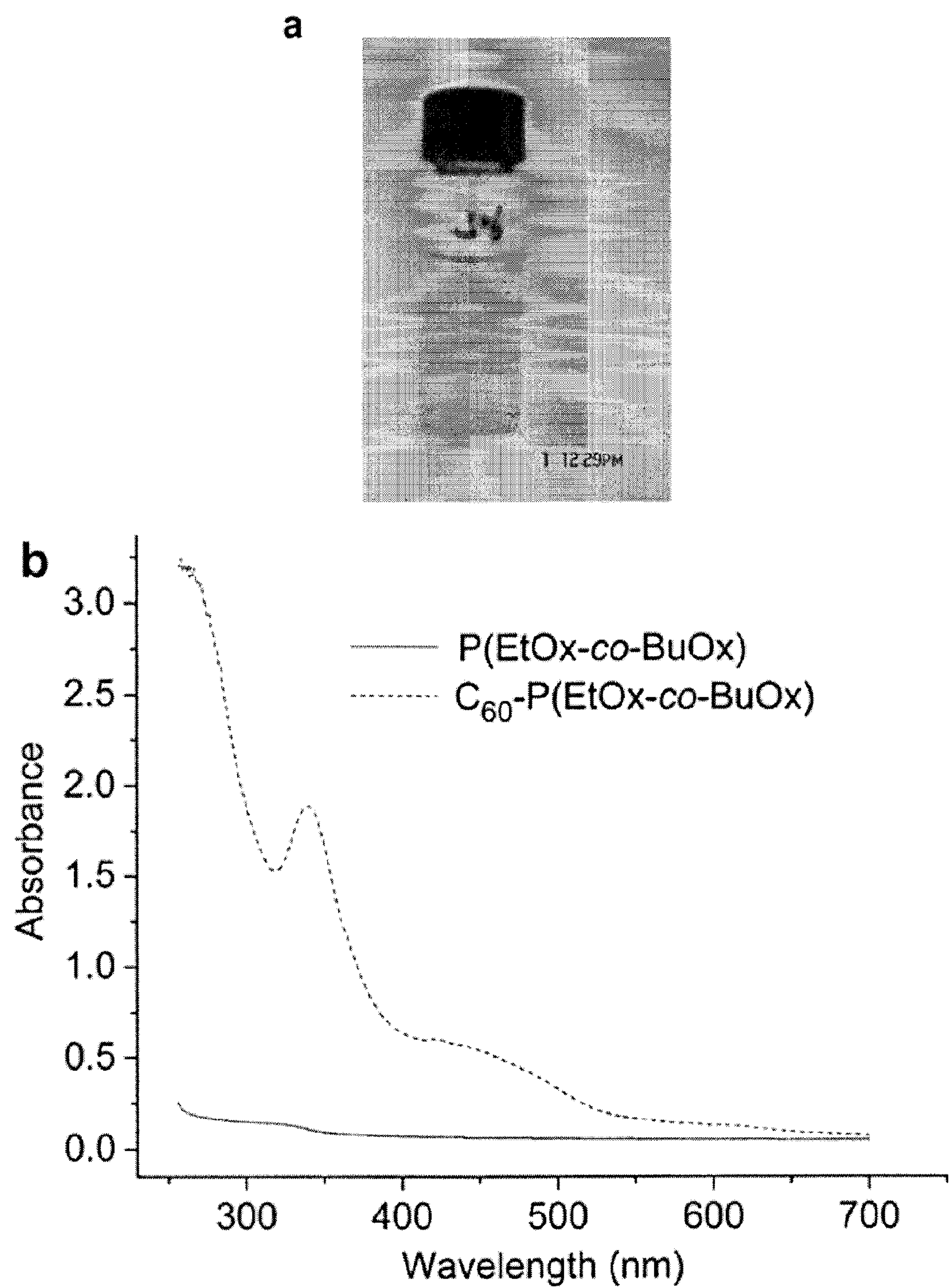
Figure 2C:
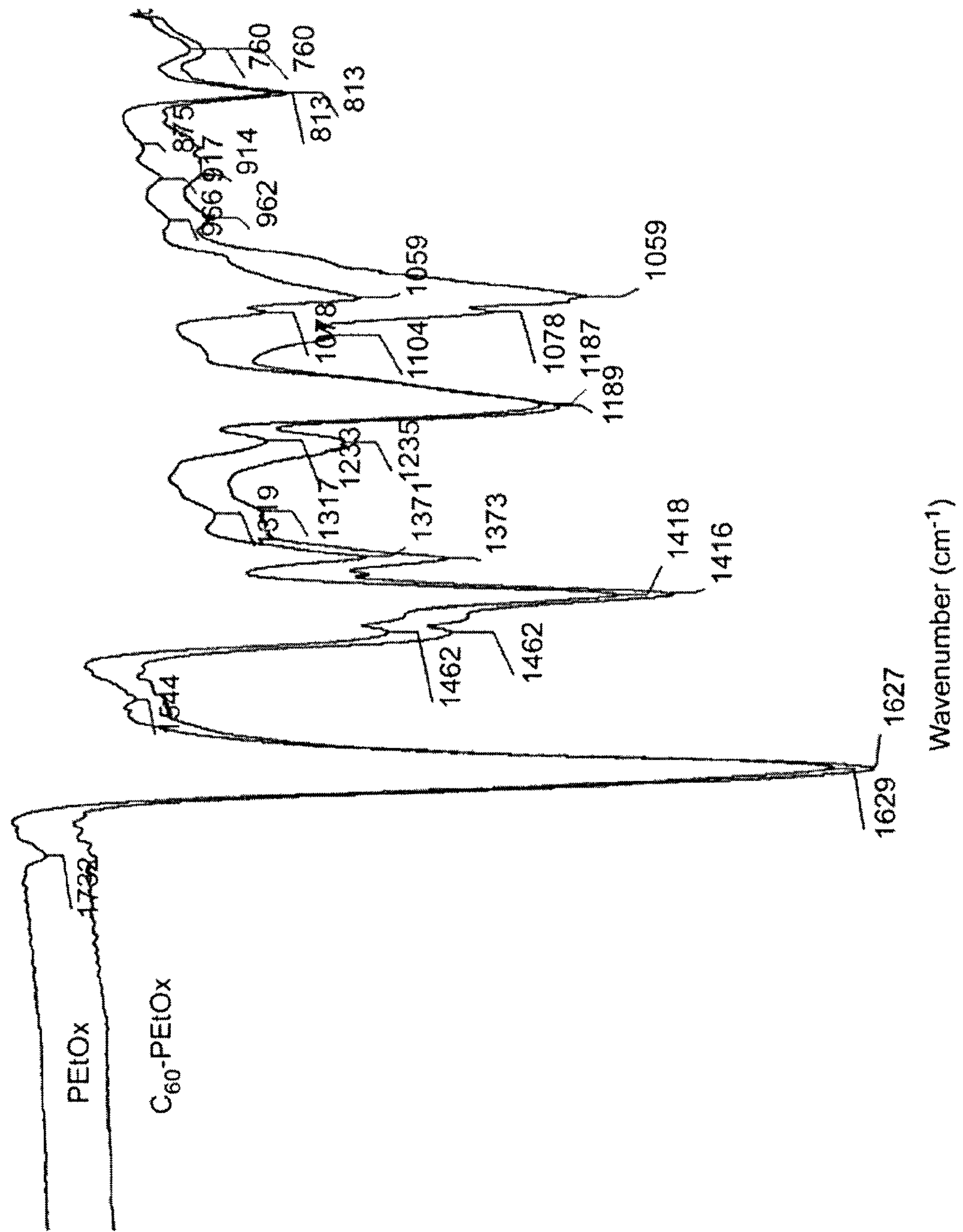
Figures 2D, 2E:
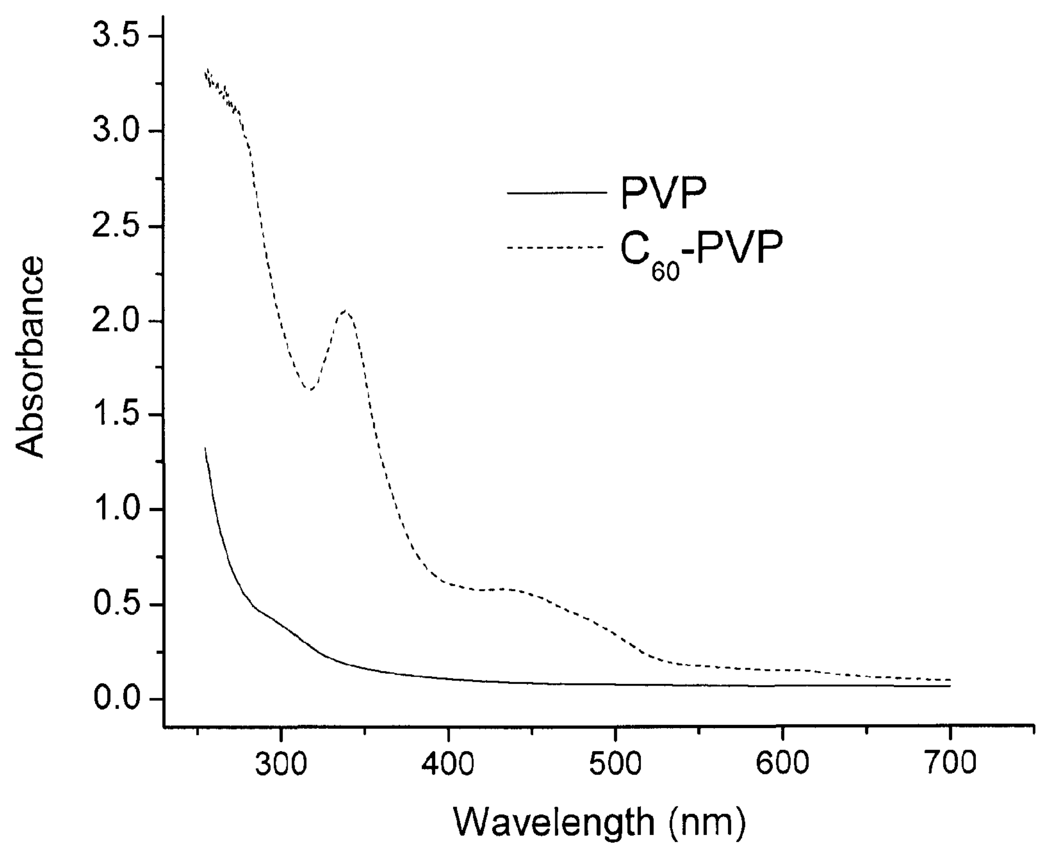

FIG. 2A provides a picture of the aqueous dispersion of $C_{60}$-P(EtOx-co-BuOx). FIG. 2B provides the UV-vis spectra of P(EtOx-co-BuOx) and $C_{60}$-P(EtOx-co-BuOx). FIG. 2C provides the infrared spectra of PEtOx and $C_{60}$-PEtOx. FIG. 2D provides a picture of the aqueous dispersion of $C_{60}$-PVP (10 kD). FIG. 2E provides the UV-vis spectra of PVP and $C_{60}$-PVP.

Figure 3A:
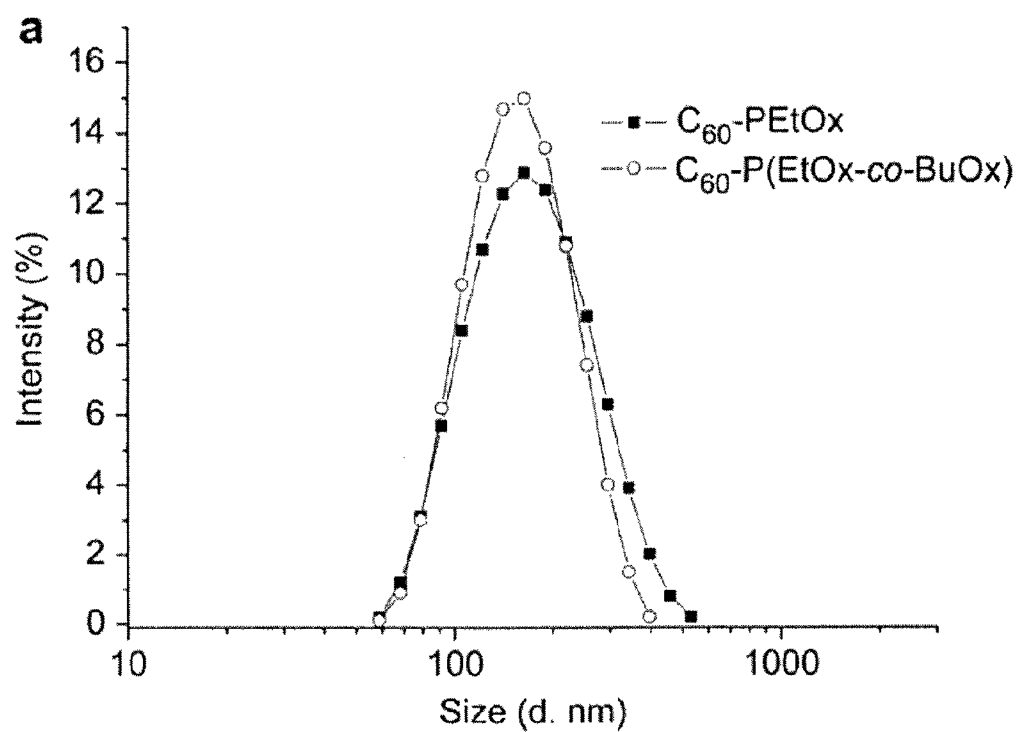
Figure 3:
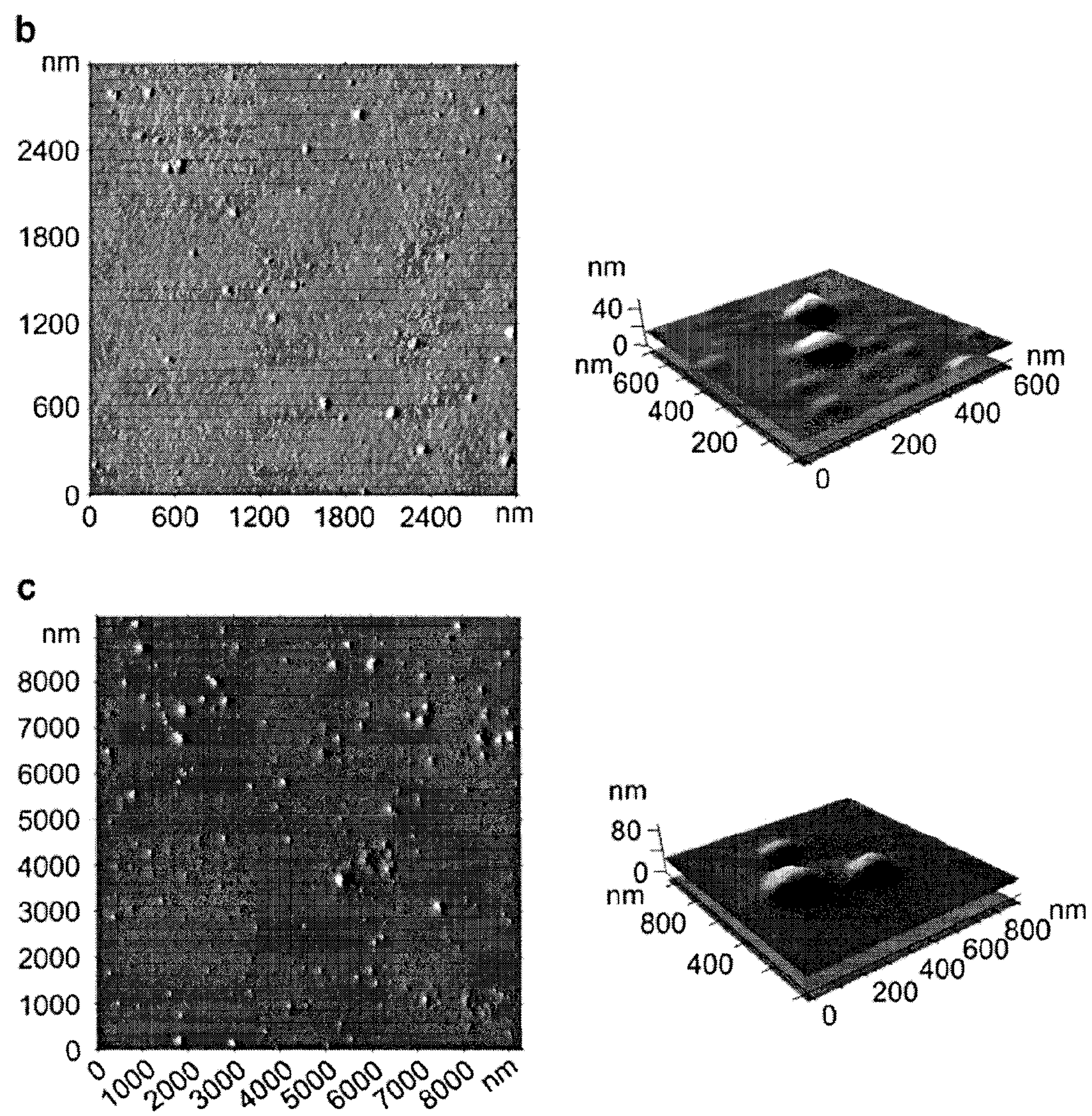
Figure 3D:
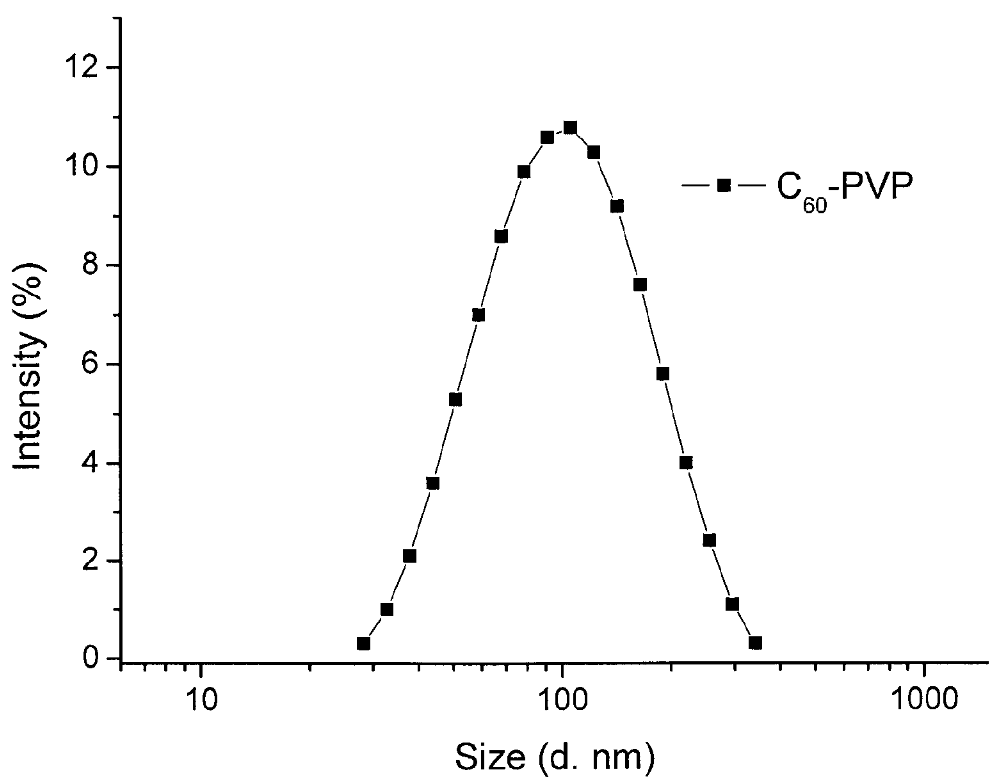
Figure 3E:
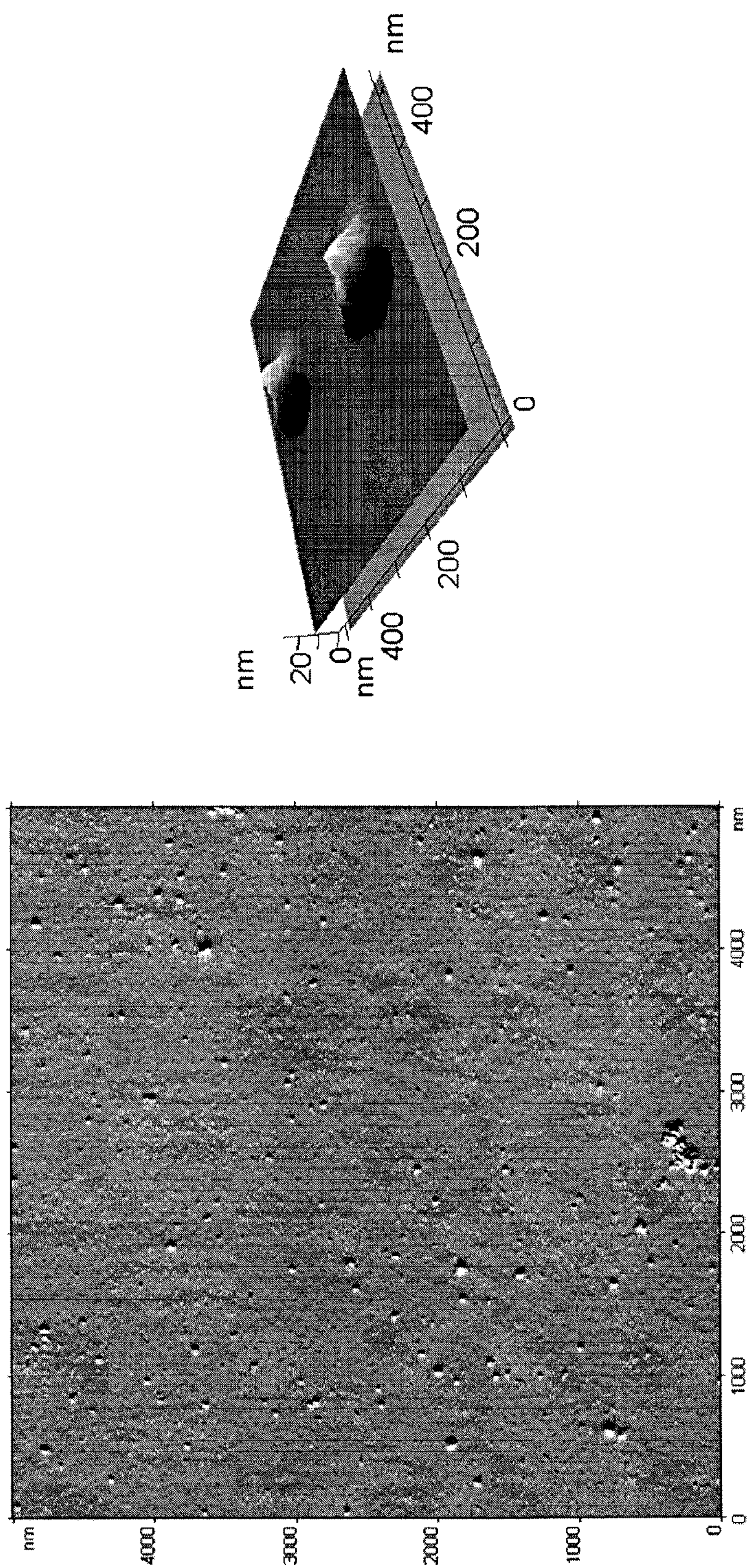

FIG. 3A provides the representative size distributions determined by dynamic light scattering (DLS) for $C_{60}$-PEtOx and $C_{60}$-P (EtOx-co-BuOx). FIGS. 3B and 3C provide atomic force microscopy (AFM) images of $C_{60}$-POx complexes: C60-PEtOx (FIG. 3B) and $C_{60}$-P(EtOx-co-BuOx) (FIG. 3C). FIGS. 3D and 3E provide the size distribution of $C_{60}$-PVP complexes determined by DLS (FIG. 3D) and AFM (FIG. 3E). For AFM, $C_{60}$-polymer complexes were deposited on the 1-(3-aminopropyl)silatrane (APS) mica. Concentration of the complexes is 100 μM in $C_{60}$.

Figure 4A:
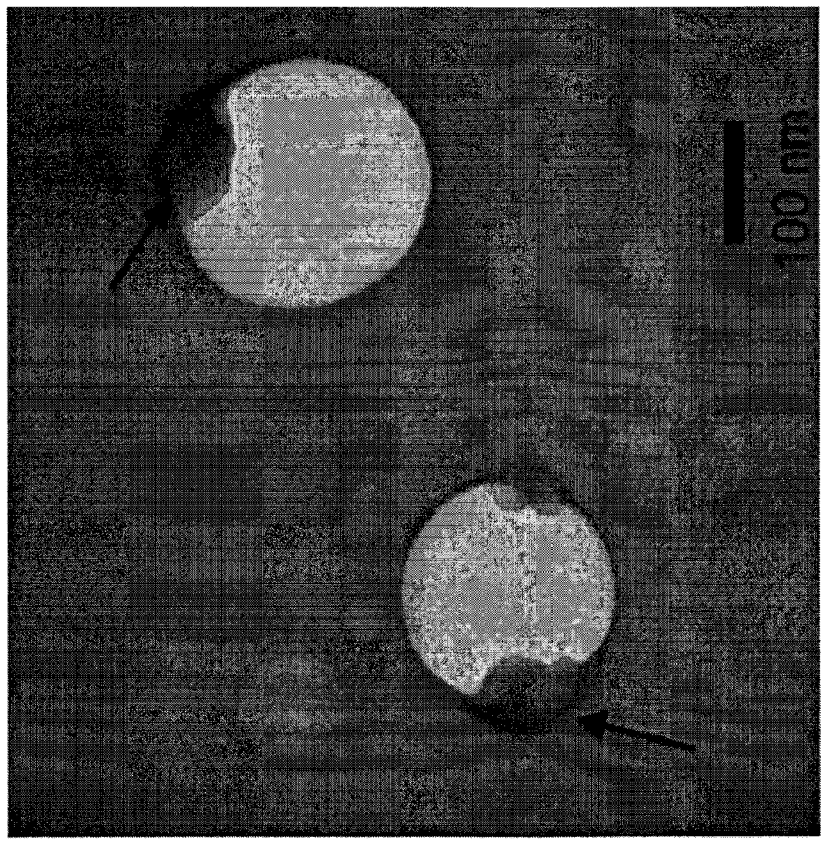
Figure 4A:
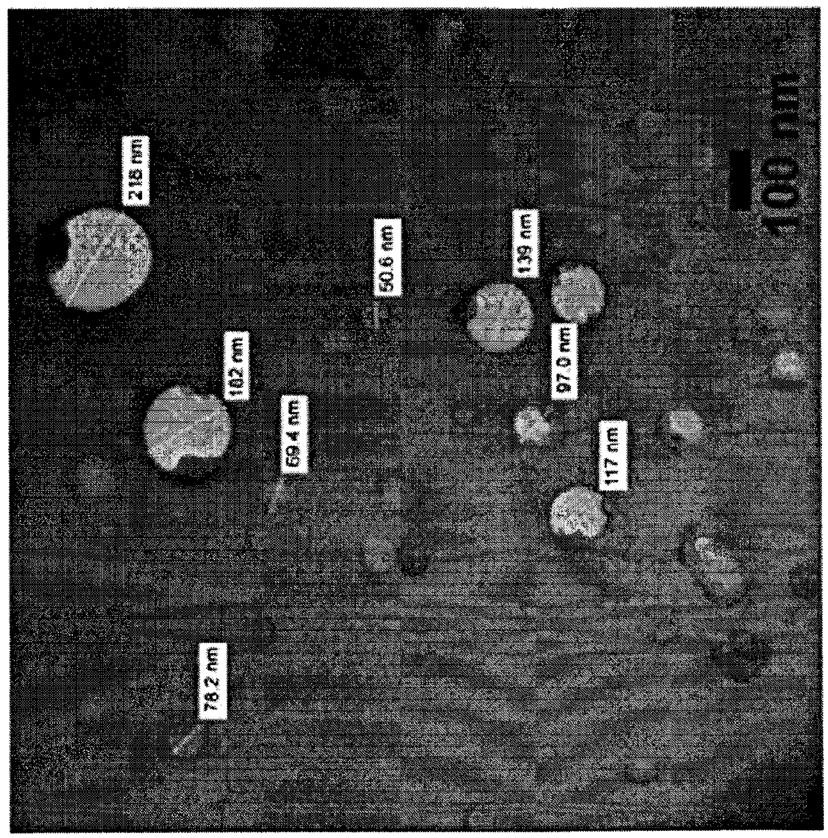
Figure 4B:
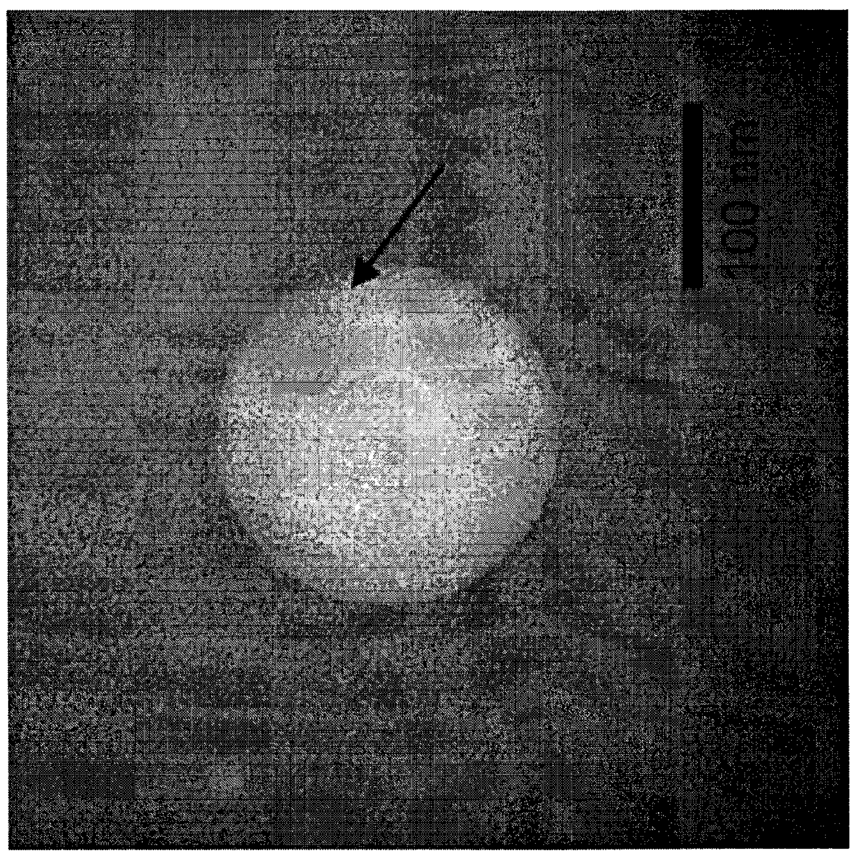
Figure 4B:
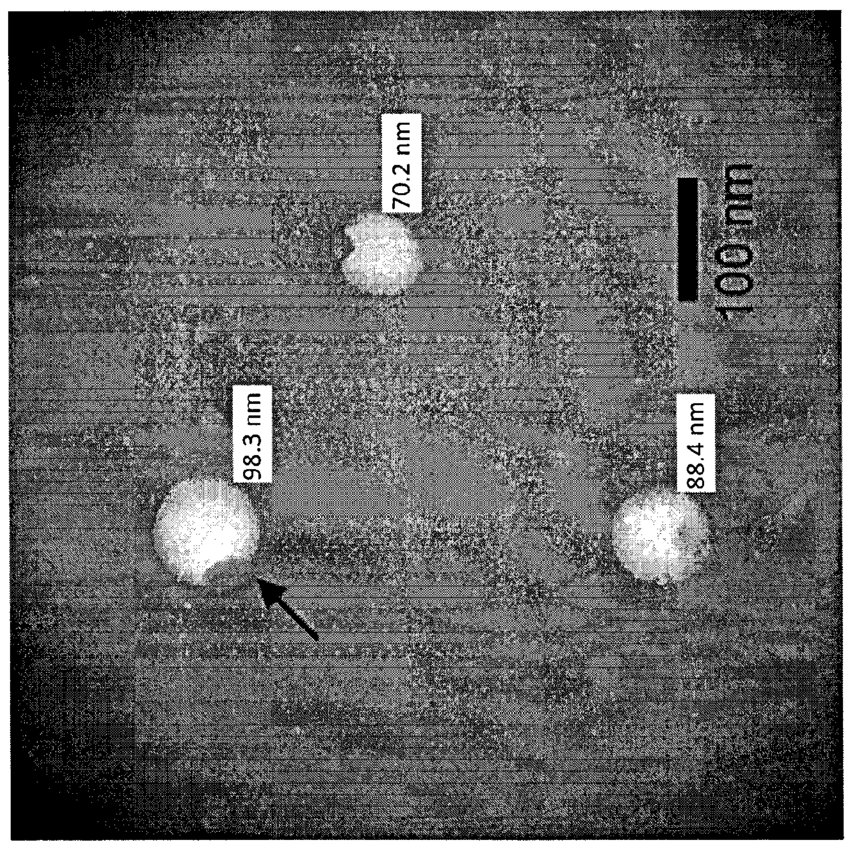

FIGS. 4A and 4B provide representative transmission electron microscopy (TEM) images of $C_{60}$-PEtOx complex (FIG. 4A) and $C_{60}$-PVP complex (FIG. 4B) obtained with negative staining using 1% of uranyl acetate. Concentration of the complex is 100 μM in $C_{60}$. The fullerene domains of the complex are marked by arrows.

Figure 5:
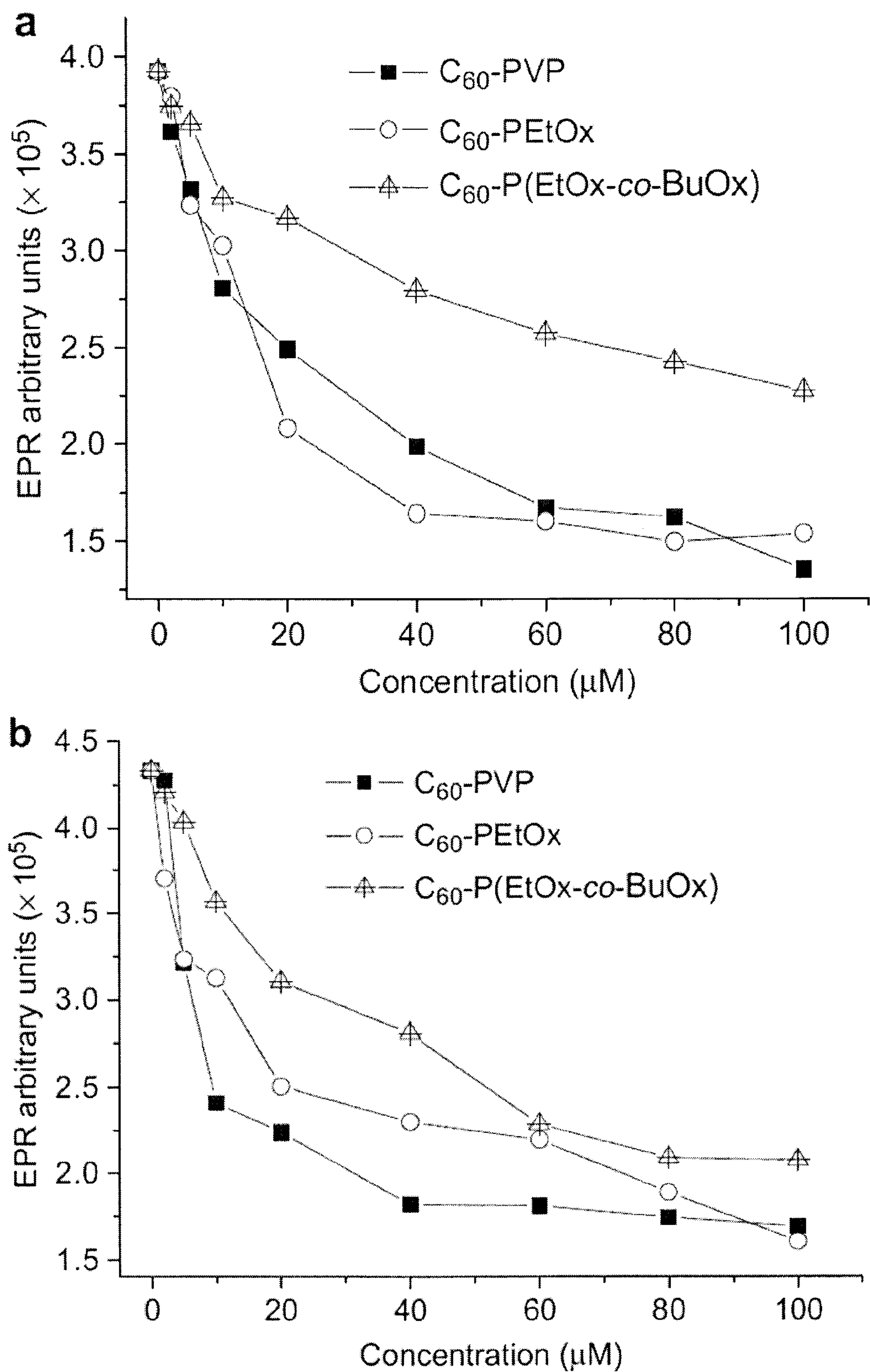
Figure 5:
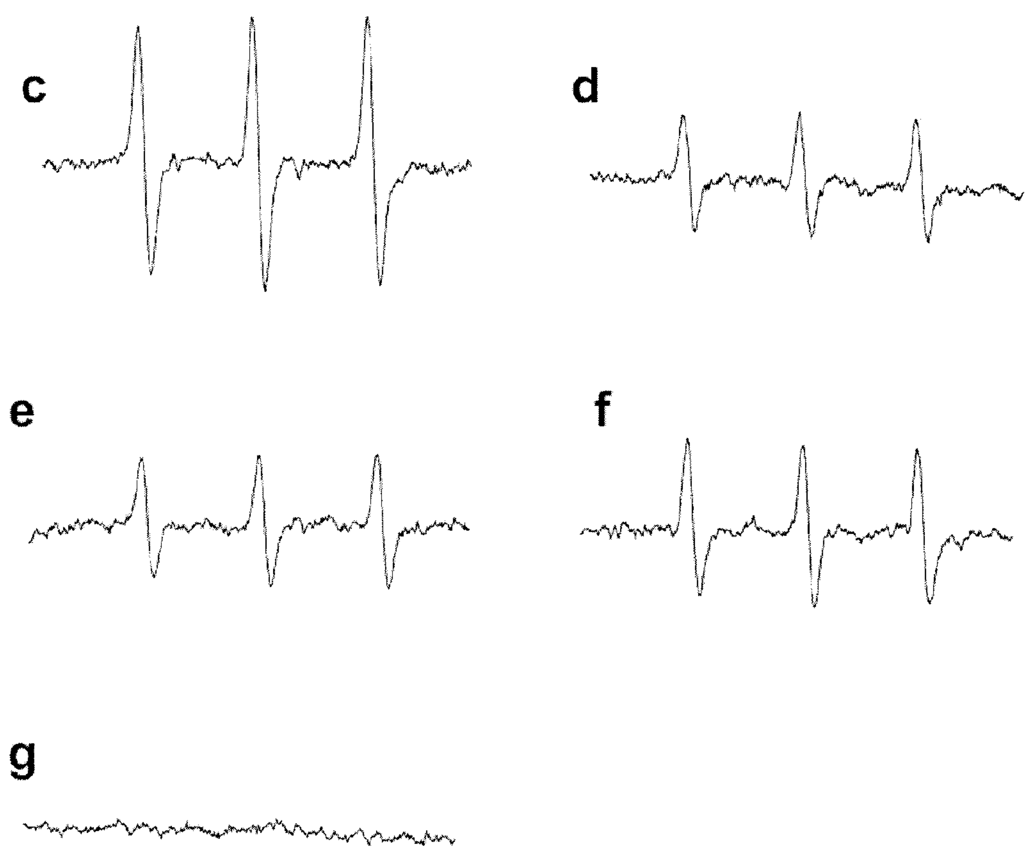

FIGS. 5A and 5B show dose-dependent superoxide scavenging by $C_{60}$-polymer complexes as determined by electron paramagnetic resonance (EPR) spectroscopy. FIG. 5A: 0.025 mM hypoxanthine (HX) and 10 mU xanthine oxidase (XO) were used as the superoxide source. FIG. 5B: 0.02 mM riboflavin 50-monophosphate sodium salt dehydrate (FMN) was used as the superoxide source. FIGS. 5C-5G provide representative EPR spectra: HX+XO alone (FIG. 5C); HX+XO in the presence of 100 μM in $C_{60}$ of $C_{60}$-PVP (FIG. 5D); HX+XO in the presence of 40 μM in $C_{60}$ of $C_{60}$-PEtOx (FIG. 5E); HX+XO in the presence of 100 μM in $C_{60}$ of $C_{60}$-P (EtOx-co-BuOx) (FIG. 5F); and HX+XO in the presence of 400 U/ml SOD1 (FIG. 5G). Each sample was incubated at room temperature for 5 minutes.

Figure 6:
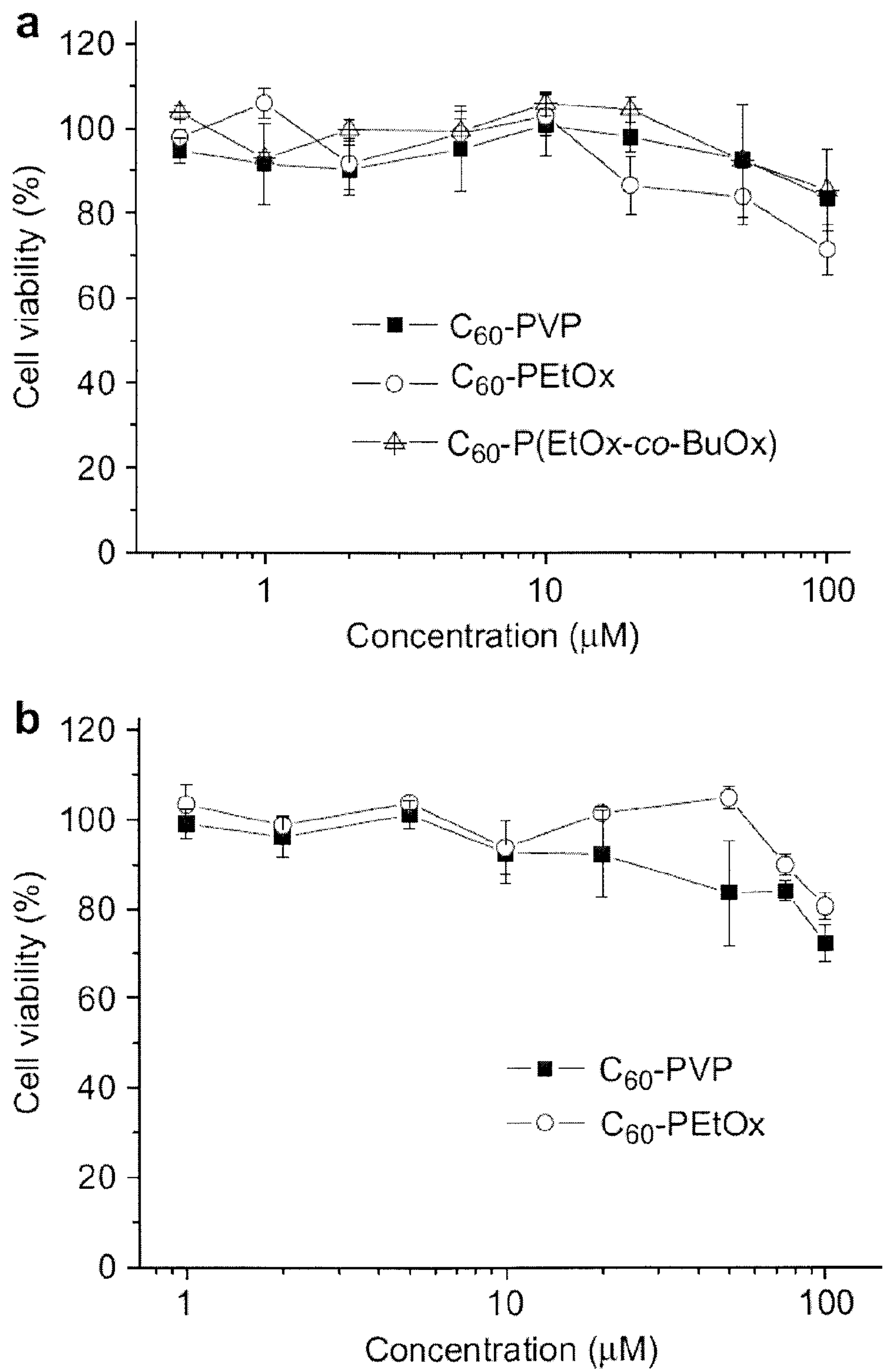
Figure 6C:
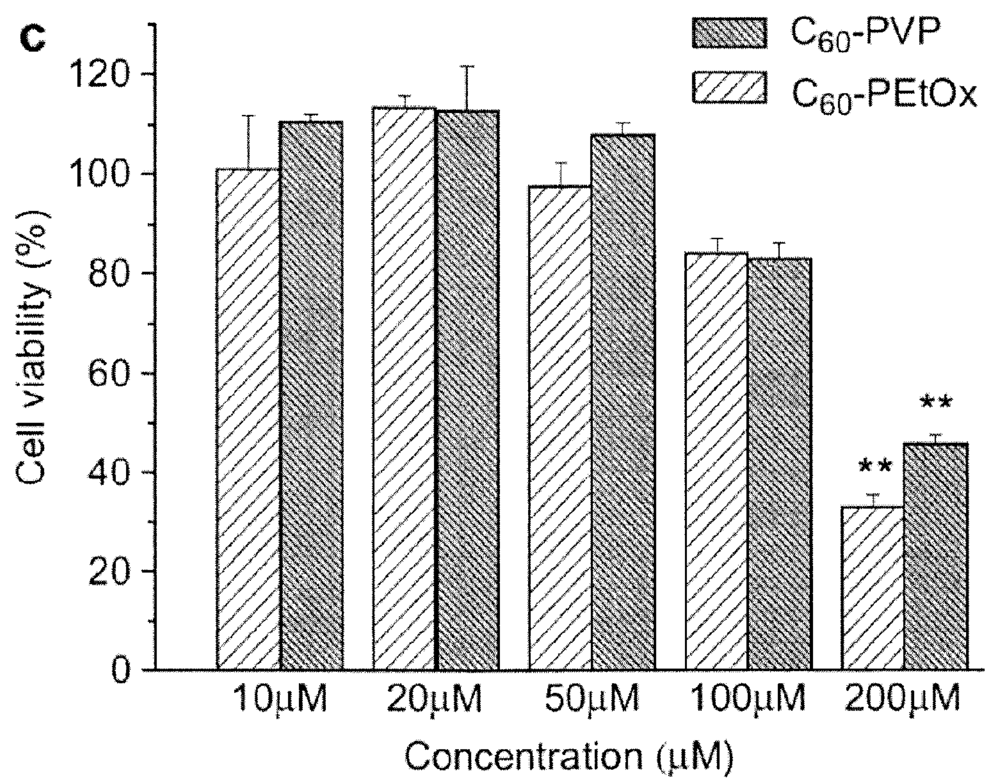

FIG. 6 provides the cytotoxicity of $C_{60}$-polymer complexes in MDCK (FIG. 6A), Hep G2 (FIG. 6B), and CATH.a neuronal cells (FIG. 6C). Cells were incubated with complexes at different concentrations of $C_{60}$ for 24 hours. Cytotoxicity was determined by the cell counting assay. **p<0.01, n=3.

Figure 7A:
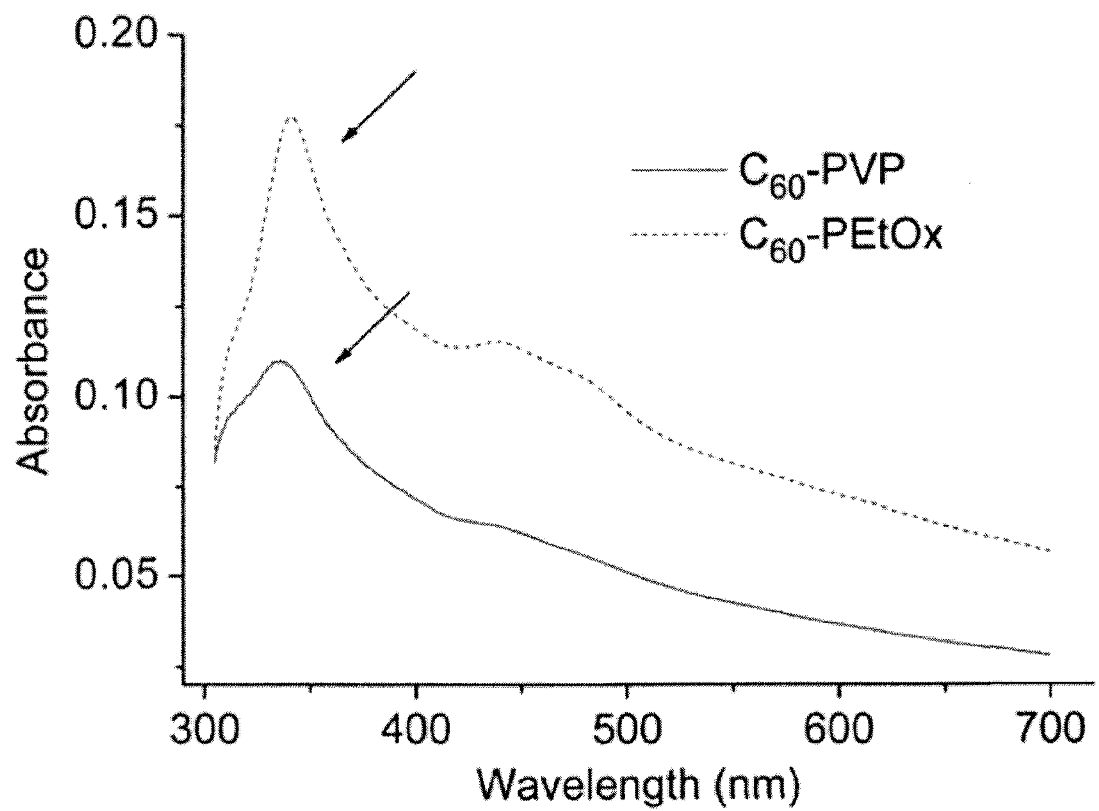
Figure 7B:
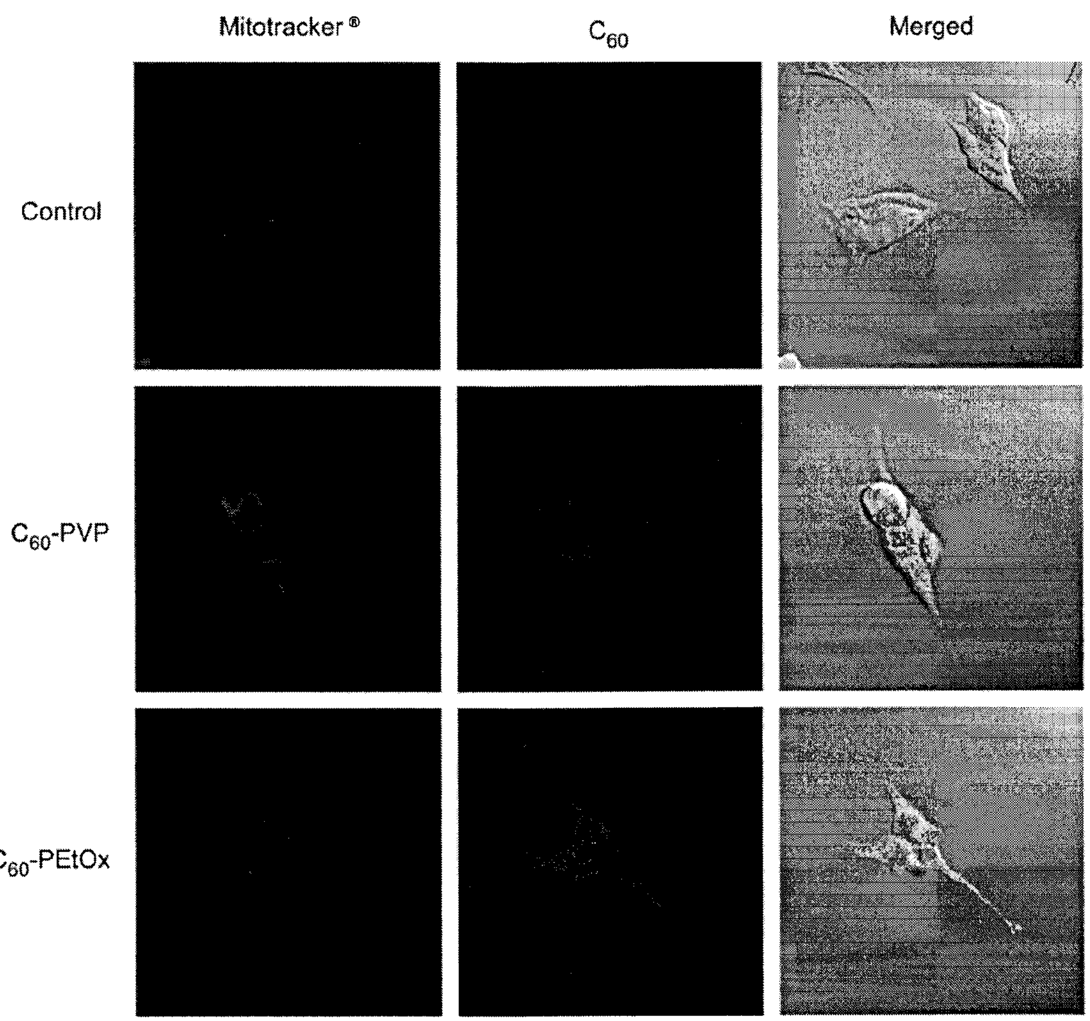
Figure 7C:
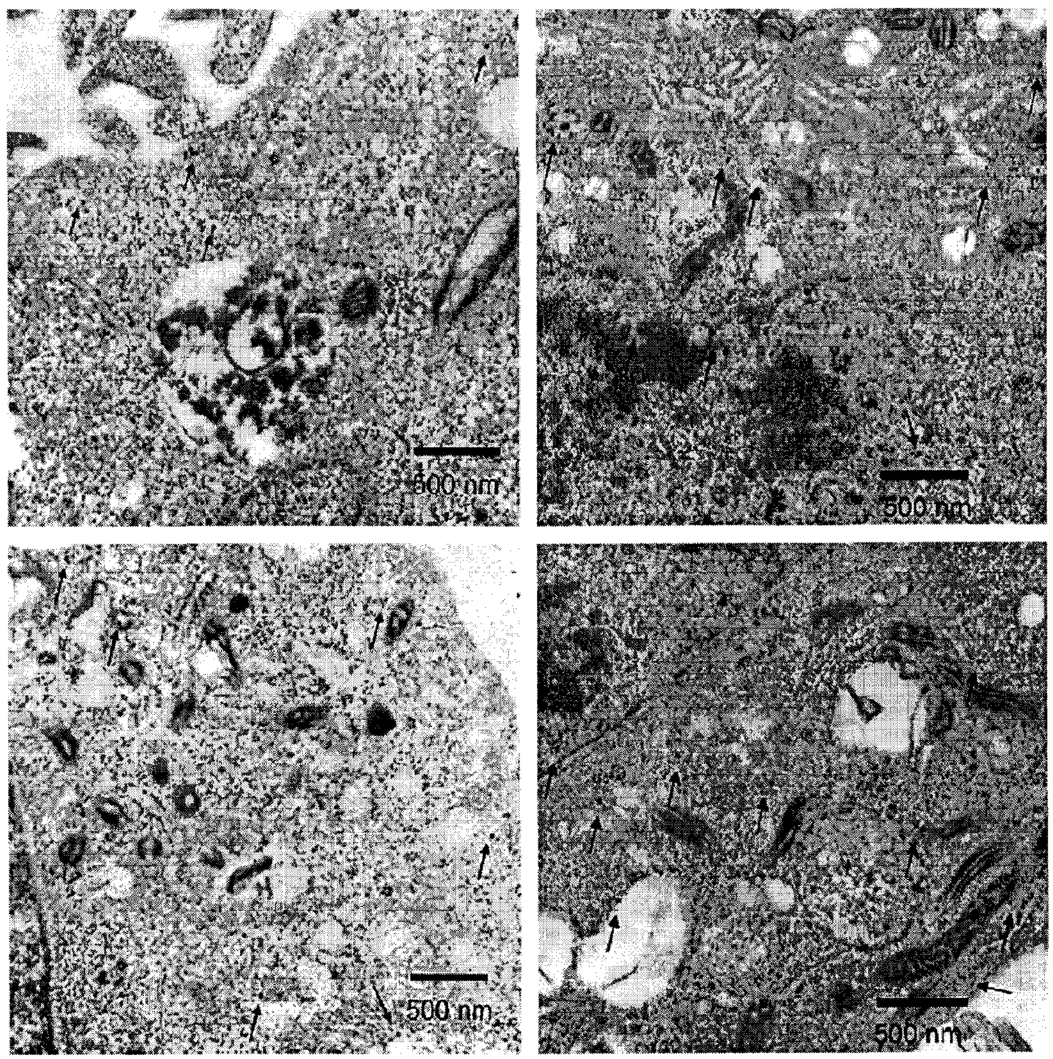

FIG. 7 shows the neuronal uptake and sub-cellular distribution of fullerene after 24 hour exposure of CATH.a neuronal cells to 100 μM $C_{60}$ complexes. FIG. 7A provides the UV-vis spectra of supernatant of cell lysates. The absorbance maximum of fullerene at 340 nm is marked by arrows. The absorbance was normalized by the cellular protein concentration determined by MicroBCA™ assay. The spectrum of the control group was subtracted. FIG. 7B provides the immunofluorescence images of CATH.a neuronal cells treated with $C_{60}$-PVP or $C_{60}$-PEtOx complexes. Cells untreated with $C_{60}$-polymer complexes are shown for comparison. Mitochondria were stained with MitoTracker® Red. Fullerene was detected with anti-fullerene antibody and then stained with Alexa Fluor® 488 labeled secondary antibody. FIG. 7C provides TEM images of CATH.a neuronal cells treated with $C_{60}$-PEtOx complex. Fullerene was detected with anti-fullerene antibody and 25 nm colloidal gold-labeled secondary antibody. The colloidal gold was marked by arrows.

Figure 8A:
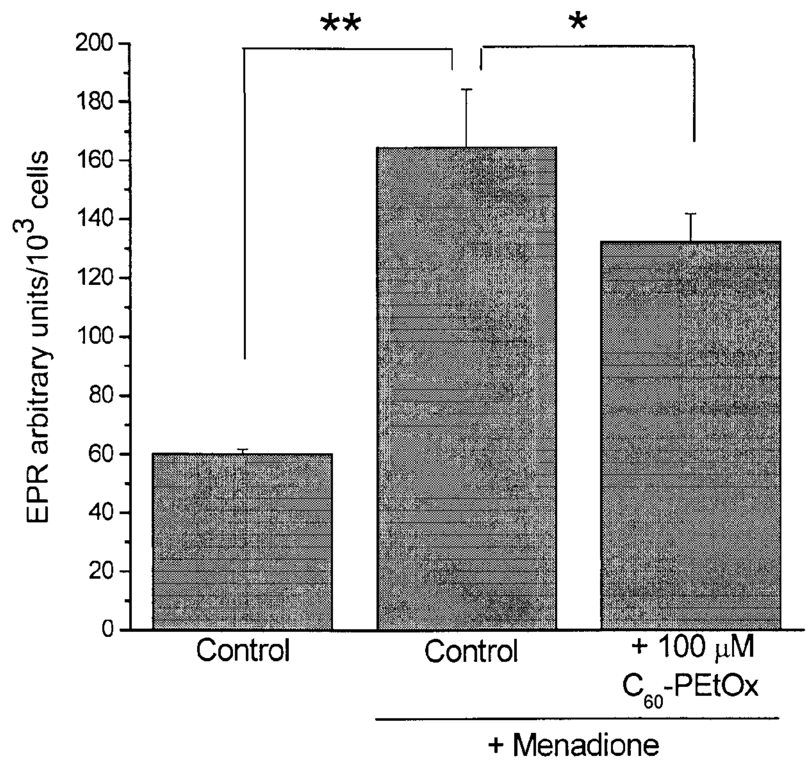
Figure 8B:
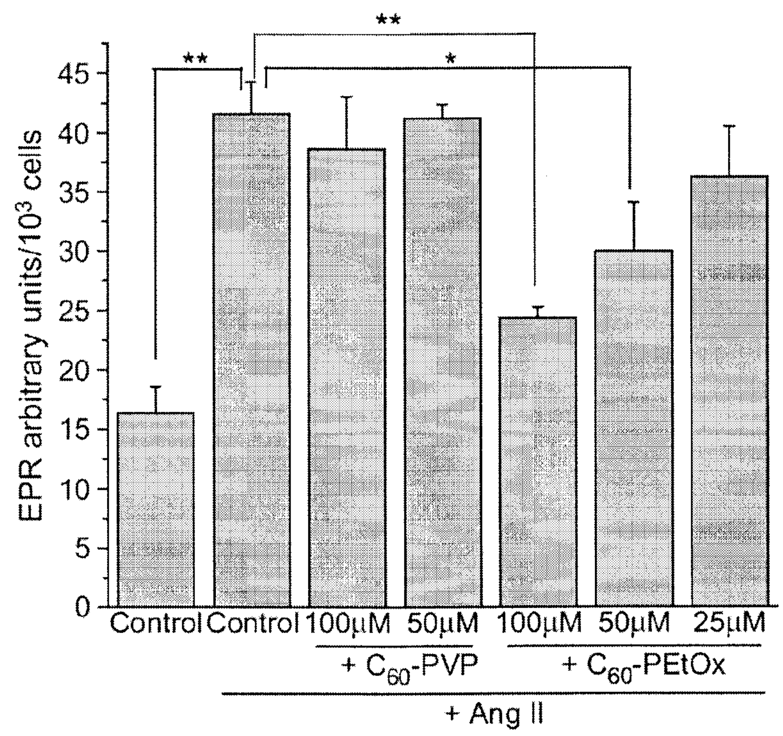

FIG. 8A shows superoxide scavenging by $C_{60}$-POx complex in CATH.a neuronal cells. Cells were treated with 100 μM of $C_{60}$-PEtOx complex for 24 hours. 200 μM of methoxycarbonyl-2,2,5,5-tetramethyl-pyrrolidine (CMH) was added as the cell-permeable spin probe. Superoxide was stimulated by treatment of cells by 20 μM of menadione for 1 hour. The signal was recorded by EPR spectroscopy over 10 minutes. EPR amplitude was normalized to total cell numbers. **p<0.01 and *p<0.05, n=3. FIG. 8B shows the intracellular superoxide scavenging by $C_{60}$-polymer complexes in CATH.a neuronal cells. CATH.a neurons were treated with various concentrations of $C_{60}$-PVP or $C_{60}$-PEtOx complexes for 24 hours. 200 μM of CMH was added as the cell-permeable spin probe. Superoxide was generated by stimulating neurons with 100 nM of Ang II. CMH radical signal was recorded by EPR spectroscopy over 10 minutes. EPR signal was normalized to total cell number. **p<0.01 and *p<0.05, n=3.

DETAILED DESCRIPTION OF THE INVENTION

Elevated levels of reactive oxygen species (ROS), including superoxide, hydroxyl radical, and hydrogen peroxide ($H_2O_2$) have been associated with the pathogenesis of numerous diseases, such as hypertension, heart failure, arthritis, cancer, and multiple neurodegenerative disorders (Pelicano et al. (2004) Drug Resist. Updat., 7:97-110; Mapp et al. (1995) Br. Med. Bull., 51:419-36; Dhalla et al. (2000) J. Hypertens., 18:655-73; Halliwell, B. (1992) J. Neurochem., 59:1609-23). More specifically, considerable evidence has shown that the intracellular signaling pathway of angiotensin II (Ang II), a vasoconstrictor peptide that increases sympathetic nerve activity causing an elevation of blood pressure, involves an increase in superoxide. In neurons, the Ang II-induced increase in superoxide modulates ion channel activity and increases neuronal excitations which are linked to neurocardiovascular diseases like hypertension and heart failure (Zimmerman et al. (2004) Prog. Biophys. Mol. Biol., 84:125-49; Welch, W. J. (2008) Hypertension 52:51-6; Laursen et al. (1997) Circulation 95:588-93; Zimmerman et al. (2005) Hypertension 45:717-23; Yin et al. (2010) Am. J. Physiol. Cell Physiol., 298:C857-65). Therefore, scavenging superoxide in the central nervous system (CNS) is a rational strategy for the treatment of Ang II-dependent cardiovascular diseases.

Fullerene, the third allotrope of carbon, has been referred to as a "radical sponge" because of its powerful radical scavenging activities. However, the hydrophobicity and toxicity associated with fullerene limits its application as a therapeutic antioxidant. Numerous water-soluble fullerene derivatives have been synthesized and exhibited excellent ROS scavenging capabilities in several disease models. Further, fullerene, as an electron-receptor, can be solubilized by polymers containing electron-donors (like amide groups) to form water-soluble charge-transfer complexes (Ungurenasu et al. (2000) J. Med. Chem., 43:3186-8). These fullerene-polymer complexes, of which $C_{60}$-PVP has been the most widely studied, usually have high aqueous solubility, high colloidal stability, narrow size distribution and low toxicity, which are suitable for biological and pharmaceutical applications (Ungurenasu et al. (2000) J. Med. Chem., 43:3186-8; Xiao et al. (2005) Biomed. Pharmacother., 59:351-8). Compared to functionalized fullerenes, the application of pristine fullerene provides ease of manufacturing, low cost, and high yield. Furthermore, evidence shows that after being properly formulated, pristine fullerene is also a therapeutic agent for ROS-related diseases and other biomedical applications. For example, the water-soluble $C_{60}$-PVP complex (Radical Sponge®) has been successfully commercialized by a Japanese company as an antioxidant for skin protection (Xiao et al. (2006) Bioorg. Med. Chem. Lett., 16:1590-5). Recently, it has also been reported that fullerene formulated with sodium dodecyl sulfate, γ-cyclodextrin or ethylene vinyl acetate-ethylene vinyl versatate copolymer can efficiently protect L929 cells from the cytotoxicity induced by nitric oxide (Misirkic et al. (2009) Biomaterials 30:2319-28). This study, however, used mechanochemical assisted formulation of $C_{60}$-based nanoparticles, usually characterized by high PDI, which is an impediment for their regulatory approval. Furthermore, it is likely that the $C_{60}$ was chemically modified due to high shear stress and energy released upon the mechanochemical formulation procedure. Therefore, efficient and biocompatible excipients allowing formulation of fullerene in mild conditions are needed to advance fullerene-based products to a broader clinical use.

Herein, the limitations of other fullerene compositions are overcome by generating water-soluble nanoformulations of fullerene. Specifically, the biocompatible polymer poly(2-alkyl-2-oxazoline)s (POx) is shown to form water-soluble, antioxidant-active complexes with fullerene. One type of $C_{60}$-PVP (PVP 10 kDa) and two types of $C_{60}$-POx (PEtOx 5 kDa, and P(EtOx-co-BuOx) 8 kDa) complexes were prepared and their physicochemical properties and superoxide scavenging activities were quantitatively measured and compared. More specifically, the $C_{60}$-polymer complexes were characterized by UV-vis spectroscopy, infrared spectroscopy (IR), dynamic light scattering (DLS), atomic force microscopy (AFM) and transmission electron microscopy (TEM). Cellular uptake and intracellular distribution of the selected formulations in catecholaminergic (CATH.a) neurons were examined by UV-vis spectroscopy, immunofluorescence and immunogold labeling. Electron paramagnetic resonance (EPR) spectroscopy was used to determine the ability of the $C_{60}$-polymer complexes to scavenge superoxide. Their cytotoxicity was evaluated in three different cell lines. $C_{60}$-POx and $C_{60}$-PVP complexes exhibited similar physicochemical properties and antioxidant activities. $C_{60}$-poly(2-ethyl-2-oxazoline) (PEtOx) complex, but not $C_{60}$-PVP complex, were efficiently taken up by CATH.a neurons and attenuated the increase in intra-neuronal superoxide induced by angiotensin II (Ang II) stimulation. These results show that $C_{60}$-POx complexes are non-toxic, neuronal cell permeable, superoxide scavenging antioxidants that can be used for the treatment of brain-related diseases associated with increased levels of superoxide.

POx polymers have been studied for their formulation, drug delivery, and other biomedical and pharmaceutical applications (Luxenhofer et al. (2010) Biomaterials 31:4972-9; Hoogenboom, R. (2009) Angew Chem. Int. Ed. Engl., 48:7978-94). PMeOx and PEtOx have shown high biocompatibility and similar properties as PEG (Gaertner et al. (2007) J. Control Release, 119:291-300). However, PEG as a polyether is prone to oxidation and can elicit oxidative stress by itself (Sung et al. (2009) J. Cell. Physiol., 218:549-57; Sung et al. (2010) Soft Matter 6:5196-205). Herein, it is demonstrated that POx can form water-soluble and biocompatible nano-complexes with fullerene. The type of polymer used in such formulations has profound effects on the physicochemical properties of the resulting $C_{60}$-based nanoparticles, as well as their intracellular uptake and superoxide scavenging ability. For example, the complex formed by a more hydrophobic POx, P(EtOx-co-BuOx), has smaller particle size and lower scavenging activity than those of $C_{60}$-PEtOx complex. Without being bound by theory, P(EtOx-co-BuOx) might form dense nanoscale networks around $C_{60}$ molecules (or clusters), which limits the accessibility of superoxide radicals to the fullerene. In contrast, a more hydrophilic PEtOx polymer may form more swollen, bulky, and accessible fullerene-based aggregates.

It has been reported that nanosized aggregates of pristine fullerene cause oxidative damage to the cell membranes and are substantially more toxic than highly water-soluble $C_{60}$ derivatives (Sayes et al. (2004) Nano Lett., 4:1881-7). It is demonstrated herein that when properly formulated with water-soluble polymers, both PVP and POx, fullerene does not exhibit any substantial toxicity in kidney, hepatocyte and neuronal cells in a broad dose range. The hydrophilic polymers used in these formulations can effectively mask fullerene from contact with cell membranes and substantially attenuate its cytotoxicity.

The pathogenesis of Ang II-dependent cardiovascular diseases, including hypertension and heart failure, involves an increase in intracellular ROS produced by NADPH oxidases and/or mitochondria (Yin et al. (2010) Am. J. Physiol. Cell. Physiol., 298:C857-65). Recent evidence has shown that fullerene may be used as a scavenger of Ang II-induced ROS in the disease conditions. For example, it has been reported that a water-soluble fullerene vesicle alleviated Ang II-induced oxidative stress in endothelial cells (Maeda et al. (2008) Hypertens. Res., 31:141-51). In the present study, $C_{60}$-PEtOx complex showed a considerable intracellular superoxide scavenging effect in CATH.a neuronal cells stimulated with 100 nM of Ang II. Notably, the previously developed $C_{60}$-PVP system was not active under the same conditions. Differential neuronal uptake is one major reason for different intracellular ROS scavenging activities of these two complexes. Indeed, the neuronal uptake of $C_{60}$-PEtOx complex is at least two times greater than that of $C_{60}$-PVP complex. The microstructures of these complexes may play an important role in the process of neuronal membrane binding and uptake. Another possible reason is that compared to PVP, POx may have more favorable interaction and non-specific binding with cell membranes. Recently it has been reported that the cellular binding and internalization of a model protein, horseradish peroxidase was significantly increased after this protein was conjugated with POx copolymers (Tong et al. (2010) Mol. Pharm., 7:984-92). In the present study, the greater uptake of $C_{60}$-PEtOx complex in neuronal cells reinforces the significance of such formulations as ROS scavengers. The analysis of intracellular distribution after 24 hours of $C_{60}$-PEtOx complex incubation with cells by TEM imaging showed that fullerene was distributed in both cytoplasm and nuclear region but not in mitochondria. Similar localization was previously found in skin keratinocytes treated with $C_{60}$-liposome complex (Kato et al. (2010) J. Photochem. Photobiol. B, 98:144-51). Notably, the distribution of POx-based fullerene complexes may be drastically different from that of some water-soluble fullerene derivatives. For example, carboxylated fullerene was localized into mitochondria and inhibited mitochondrial ROS formation (Chirico et al. (2007) Exp. Dermatol., 16:429-36; Foley et al. (2002) Biochem. Biophys. Res. Commun., 294: 116-9). Here, the lack of mitochondrial localization indicates that $C_{60}$-PEtOx complex can efficiently scavenge the ROS stimulated in the cytoplasm. Indeed, $C_{60}$-PEtOx efficiently scavenged 60% of superoxide induced by Ang II stimulation, but only 20-30% of superoxide induced by menadione. This may be explained by different mechanisms of action of these two ROS generators. It is well known that Ang II induces the increase of superoxide in both cytoplasm and mitochondria, while menadione generates superoxide via redox cycling in the mitochondrial electron transport chain (Zimmerman, M. C. (2004) Prog. Biophys. Mol. Biol., 84:125-49; Yin et al. (2010) Am. J. Physiol. Cell. Physiol., 298:C857-65; Cadenas et al. (2000) Free Radic. Biol. Med., 29:222-30). Altogether, the data indicates that POx-based fullerene formulations are stable, biocompatible and efficient superoxide scavengers in neuronal cells.

In the present study, new types of $C_{60}$-polymer complexes were prepared and characterized by various techniques. Their physicochemical properties, antioxidant activities and cytotoxicity were evaluated and compared. The results show that $C_{60}$-PEtOx exhibited greater cellular uptake and significant intracellular superoxide scavenging activity in CATH.a neuronal cells, which is not found in $C_{60}$-PVP complex. Efficient scavenging of intracellular superoxide induced by Ang II stimulation indicates the therapeutic use of $C_{60}$-POx complexes in Ang II-related cardiovascular diseases like hypertension and heart failure. It is also noteworthy that the safety of POx has been validated and the homopolymer PEtOx has been applied as an excipient in cosmetic industry. Therefore, this study also highlights the applications of $C_{60}$-POx complexes as cosmetic formulations and treatments of other ROS-related human diseases.

I. Compositions

In accordance with the instant invention, compositions are provided comprising at least one fullerene (e.g., at least one type) and at least one oxazoline polymer. In a particular embodiment, the fullerene and oxazoline polymer are complexed to form nanoparticles. The compositions may further comprise at least one carrier, particularly a pharmaceutically acceptable carrier.

As used herein, the term "fullerene" refers to a molecule containing carbon atoms arranged in a closed cage. Fullerenes may comprise from 20 to about 500 or more carbon atoms, particularly from 60 to 200 carbon atoms. In a general notation, $C_x$ represents a fullerene cage having x carbon atoms. Fullerenes are typically spherical, but may form other shapes such as carbon nanotubes. For example, the fullerene may be a tubular structure with hemispherical caps at each end of the tube. Examples of fullerenes include, without limitation, $C_{60}$, $C_{70}$, $C_{76}$, $C_{82}$, $C_{84}$, $C_{96}$, $C_{240}$, and $C_{540}$. In a particular embodiment, the fullerene is $C_{60}$ and/or $C_{70}$. The fullerene may comprise chemical moieties attached to the exterior or incorporated within the cage. In a particular embodiment, the fullerene is pristine fullerene.

The instant invention may also encompass the use of hyperfullerenes in place of the fullerene. Hyperfullerenes comprise one or more fullerene molecules inside another, i.e., hyperfullerene structures comprise one structure contained within a second larger structure.

The compositions of the instant invention may comprise about 0.01% to about 10% (w/w) fullerene, particularly about 0.1% to about 5% fullerene, more particularly about 0.5% to about 1.0% fullerene.

In a particular embodiment, the particles of the instant invention (fullerene plus polymer) have an average size about 50 nm to about 500 nm, particularly about 100 nm to about 200 nm. In a particular embodiment, the particles of the instant invention have a narrow size distribution. For example, the particles may have a polydispersity index (PDI) of about 0.15-about 0.25.

The compositions of the instant invention may further comprise at least one therapeutic agent. The core of pristine fullerene is hydrophobic and can be used to carrier hydrophobic therapeutic agents. In a particular embodiment, the fullerene is derivatized with a linker or moiety, e.g., a hydrophilic moiety, to allow for the attachment of therapeutic agents. Therapeutic agents include, without limitation, polypeptides, peptides, glycoproteins, nucleic acids, synthetic and natural drugs, peptoides, polyenes, macrocyles, glycosides, terpenes, terpenoids, aliphatic and aromatic compounds, small molecules, and their derivatives and salts. While the therapeutic agents are exemplified herein, any bioactive agent may be administered to a patient, e.g., a diagnostic or imaging agent.

As stated hereinabove, the fullerene of the instant invention is complexed with at least one oxazoline polymer. In a particular embodiment, the oxazoline polymer is a water-soluble, biocompatible polymer. The fullerene may be formulated with a poly(2-oxazoline) (POx) homopolymer (e.g., poly(2-alykyl-2-oxazoline)s such as poly(2-ethyl oxazoline; PEtOx) or an oxazoline copolymer (e.g., P(EtOx-co-BuOx)). Examples of oxazoline polymers are provided in PCT/US11/31542

The oxazoline copolymer may be a random copolymer or a block copolymer. Block copolymers are most simply defined as conjugates of at least two different polymer segments. The simplest block copolymer architecture contains two segments joined at their termini to give an A-B type diblock. Consequent conjugation of more than two segments by their termini yields A-B-A type triblock, A-B-A-B-type multiblock, or even multisegment A-B-C-architectures. If a main chain in the block copolymer can be defined in which one or several repeating units are linked to different polymer segments, then the copolymer has a graft architecture of, e.g., an $A(B)_n$ type. More complex architectures include for example $(AB)_n$ (wherein m is about 1 to about 100) or $A_nB_m$ starblocks which have more than two polymer segments linked to a single center. An exemplary block copolymer of the instant invention has the formula A-B or B-A, wherein A is a hydrophilic polymer segment and B is a hydrophobic polymer segment. Another exemplary block copolymer has the formula A-B-A. Block copolymers structures include, without limitation, linear copolymers, star-like block copolymers, graft block copolymers, dendrimer based copolymers, and hyperbranched (e.g., at least two points of branching) block copolymers. The segments of the block copolymer may have from about 2 to about 1000, about 2 to about 300, or about 2 to about 100 repeating units or monomers.

Well-defined poly(2-oxazoline) block copolymers of the instant invention may be synthesized by the living cationic ring-opening polymerization of 2-oxazolines. The synthetic versatility of poly(2-oxazoline)s allows for a precise control over polymer termini and hydrophilic-lipophilic balance (HLB). Block length, structure, charge, and charge distribution of poly(2-oxazoline)s may be varied. For example, the size of the hydrophilic and/hydrophobic blocks may be altered, triblock polymers may be synthesized, star-like block copolymers may be used, polymer termini may be altered, and ionic side chains and/or ionic termini may also be incorporated. Ionic side chains (e.g., comprising —R—$NH_2$ or R—COOH, wherein R is an alkyl) may be incorporated into the hydrophilic (preferably) or hydrophobic block. The polymers of the instant invention may also comprise units or blocks from other polymers (e.g., hybrid oxazoline polymers) such as polyethyleneoxide (PEG), polyester, polylactic acid, poly(lactide-co-glycolide), poly(lactic-co-glycolic acid), poly(acrylic acid), poly(methacrylic acid), poly(ethyleneimine), polycaprolactone, chitosan, poly(2-(N,N-dimethylamino)ethyl methacrylate), or polyamino acid (e.g. polyaspartate, poly(glutamic acid), poly(lysine) or poly(aspartic acid)).

Poly(2-oxazoline)s (also known as 2-substituted 4,5-dihydro oxazoles) are polysoaps and depending on the residue at the 2-position of the monomer can be hydrophilic (e.g., methyl, ethyl) or hydrophobic (e.g. propyl, pentyl, nonyl, phenyl, and the like) polymers. Moreover, numerous monomers introducing pending functional groups are available (Taubmann et al. (2005) Macromol. Biosci., 5:603; Cesana et al. (2006) Macromol. Chem. Phys., 207:183; Luxenhofer et al. (2006) Macromol., 39:3509; Cesana et al. (2007) Macromol. Rapid Comm., 28:608). Poly(2-oxazoline)s can be obtained by living cationic ring-opening polymerization (CROP), resulting in well-defined block copolymers and telechelic polymers of narrow polydispersities (Nuyken, et al. (1996) Macromol. Chem. Phys., 197:83; Persigehl et al. (2000) Macromol., 33:6977; Kotre et al. (2002) Macromol. Rapid Comm., 23:871; Fustin et al. (2007) Soft Matter, 3:79; Hoogenboom et al. (2007) Macromol., 40:2837). Several reports indicate that hydrophilic poly(2-oxazoline)s are essentially non-toxic and biocompatible (Goddard et al, (1989) J. Control. Release, 10:5; Woodle et al. (1994) Bioconjugate Chem., 5:493; Zalipsky et al. (1996) J. Pharm. Sci., 85:133; Lee et al. (2003) J. Control. Release, 89:437; Gaertner et al. (2007) J. Control. Release, 119:291). Using lipid triflates or pluritriflates, lipopolymers (Nuyken, et al. (1996) Macromol. Chem. Phys., 197:83; Persigehl et al. (2000) Macromol., 33:6977; Kotre et al. (2002) Macromol. Rapid Comm., 23:871; Fustin et al. (2007) Soft Matter, 3:79; Hoogenboom et al. (2007) Macromol., 40:2837; Punucker et al. (2007) Soft Matter, 3:333; Garg et al. (2007) Biophys. J., 92:1263; Punucker et al. (2007) Phys. Rev. Lett., 98:078102/

1; Luedtke et al. (2005) Macromol. Biosci., 5:384; Purmcker et al. (2005) J. Am. Chem. Soc., 127:1258) or star-like poly (2-oxazoline)s are readily accessible. Additionally, various poly(2-oxazoline)s with terminal quaternary amine groups have been reported, which interact strongly with bacterial cell membranes (Waschinski et al. (2005) Macromol. Biosci., 5:149; Waschinski et al. (2005) Biomacromol., 6:235).

The copolymers of the instant invention may comprise hydrophilic and hydrophobic oxazolines. Examples of hydrophilic 2-oxazolines include, without limitation, 2-methyl-2-oxazoline, 2-ethyl-2-oxazoline, and mixtures thereof. Examples of hydrophobic 2-oxazolines include oxazolines with hydrophobic substituents (e.g., an alkyl or an aryl) at the 2-position of the oxazoline ring including, without limitation 2-butyl-2-oxazoline, 2-propyl-2-oxazoline, and mixtures thereof. In a particular embodiment, the biocompatible, water soluble polymer is a homopolymer of 2-ethyl-2-oxazoline or a copolymer (random or block) comprising 2-ethyl-2-oxazoline. In a particular embodiment, the copolymer is at least as hydrophilic as the P(EtOx-co-BuOx) polymer of the instant invention or as hydrophilic as the 2-ethyl-2-oxazoline homopolymer.

In a particular embodiment of the instant invention, the polymer of the instant invention is represented by the formula provided in FIG. 1B, wherein R (e.g., an alkyl) is a singular entity for a homopolymer or varies for a copolymer (random or block). When the copolymer is a block copolymer, the polymer comprises the formula:

(I)

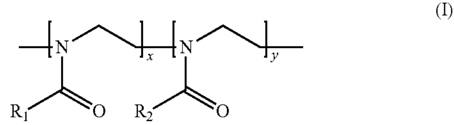

wherein x and y are independently selected between 1 and about 300, particularly about 5 to about 150, and more particularly about 10 to about 100; and wherein $R_1$ and $R_2$ are an alkyl. In a particular embodiment, $R_1$ or $R_2$ is —$CH_2CH_3$. In a particular embodiment, $R_1$ or $R_2$ is butyl (including isopropyl, sec-butyl, or tert-butyl) or propyl (including isopropyl). In yet another embodiment, $R_1$ or $R_2$ is —$CH_2$—$CH_2$—$CH_2$—$CH_3$ or —$CH_2$—$CH_2$—$CH_3$.

II. Methods

The compositions of the instant invention efficiently scavenge reactive oxygen species (ROS) and intracellular superoxide. Notably, the particles exhibit considerably high cellular uptake in neuron cells and efficiently attenuate the increase of intracellular superoxide level induced by different free radical stimulants including angiotensin II and menodione. Accordingly, the compositions of the instant invention attenuate the oxidative stress induced by different stimulants and can be used as effective antioxidant therapies.

In accordance with the instant invention, methods are provided for the treatment of reactive oxygen species (ROS)-related diseases. Elevated levels of reactive oxygen species (ROS), including superoxide, hydroxyl radical, and hydrogen peroxide ($H_2O_2$) have been associated with the pathogenesis of numerous diseases, such as hypertension, heart failure, arthritis, cancer, neurodegenerative disorders, and cardiovascular diseases (e.g., angiotensin-II induced cardiovascular diseases). The instant invention encompasses methods of inhibiting, treating, and/or preventing oxidative stress associated diseases or disorders (caused by reactive oxygen species (ROS)) comprising the administration of at least one composition of the instant invention to a subject in need thereof. In a particular embodiment, the oxidative stress associated disease or disorder is selected from the group consisting of atherosclerosis, ischemia/reperfusion injury, stroke, traumatic brain injury, restenosis, hypertension (including in chronic heart failure), heart failure, cardiovascular diseases, cancer, inflammation, an inflammatory disease or disorder, an acute respiratory distress syndrome (ARDS), asthma, inflammatory bowel disease (IBD), a dermal and/or ocular inflammation, arthritis, metabolic disease or disorder, obesity, diabetes, neurological disorders and other disorders of the central nervous system, multiple sclerosis, neurocardiovascular disease/dysregualtion, and neurodegenerative disease or disorder (e.g., Alzheimer's disease, Huntington's disease, Parkinson's disease, Lewy Body disease, amyotrophic lateral sclerosis, and prion disease). The compositions of the instant invention may also be used for immune enhancement and as an anti-aging agent.

In a particular embodiment, the method comprises administering at least one other antioxidant to the subject. The additional antioxidant may be administered simultaneously or consecutively with the compositions of the instant invention. The additional antioxidant may be in the same composition as the particles of the instant invention or contained in separate compositions (e.g., with its own carrier). The instant invention encompasses a kit comprising at least one first composition comprising the particles of the instant invention and at least one second composition comprising an additional antioxidant.

In accordance with another aspect of the instant invention, cosmetic compositions are provided comprising at least one fullerene, at least one oxazoline polymer, and at least one cosmetically acceptable carrier (e.g., for topical administration). In a particular embodiment, the fullerene containing particles of the instant invention are used in the cosmetic compositions described in U.S. Patent Application Publication No. 2005/0136079. The topical compositions of the present invention may be made into a wide variety of product types such as, without limitation, liquids, lotions, powders, creams, salves, gels, milky lotions, sticks, sprays (e.g., pump spray), aerosols, ointments, pastes, mousses, dermal patches, controlled release devices, and other equivalent forms. The instant invention also encompasses methods of inhibiting, treating, and/or preventing oxidative stress associated diseases or disorders (e.g., of the skin; for reducing damage by free radicals) through the topical application of a composition of the instant invention.

As stated hereinabove, the topical compositions of the instant invention may comprise the fullerene/polymer particles of the instant invention and at least one cosmetically acceptable carrier. "Cosmetically acceptable" refers to entities and compositions that are physiologically tolerable and do not typically produce an allergic or similar untoward reaction when administered to an animal, particularly a human. A cosmetically acceptable carrier may be a pharmaceutically acceptable carrier. Cosmetically acceptable carriers are preferably approved by a regulatory agency of the Federal or a state government. General types of acceptable topical carriers include, without limitation, emulsions (e.g., microemulsions and nanoemulsions), gels (e.g., an aqueous, alcohol, alcohol/water, or oil (e.g., mineral oil) gel using at least one suitable gelling agent (e.g., natural gums, acrylic acid and acrylate polymers and copolymers, cellulose derivatives (e.g., hydroxymethyl cellulose and hydroxypropyl cellulose), and hydrogenated butylene/ethylene/styrene and hydrogenated ethylene/propylene/styrene copolymers), solids (e.g., a wax-based stick, soap bar composition, or powder (e.g., bases such as talc, lactose, starch, and the like), liposomes (e.g., unilamellar, multilamellar, and paucilamellar liposomes, optionally containing phospholipids), stabilizers, penetration enhancers, chelating agents (e.g., EDTA, EDTA derivatives (e.g., disodium EDTA and dipotassium EDTA), iniferine, lactoferrin, and citric acid), and excipients.

The topical (cosmetic) compositions of the invention may further comprise at least one additional agent. The additional agents include, without limitation, sunscreens (e.g., organic or inorganic sunscreens such as cinnamate compounds (e.g., methoxyoctylcinnamate), titanium dioxide, zinc oxide, iron oxide, zirconium oxide, p-aminobenzoic acid, anthranilates, salicylate esters, dihydroxycinnamic acids, trihydroxy-cinnamic acids, diphenylbutadiene, stilbene, dibenzalacetone, benzalacetophenone, naphtholsulfonates, di-hydroxynaphthoic acids, o- and p-hydroxybiphenyl disulfonates, coumarin derivatives, diazoles, quinine salts, quinoline derivatives, hydroxy- or methoxy-substituted benzophenones, uric and violuric acids, tannic acids, hydroquinone, benzophenones, and derivatives and salts thereof), anti-aging agents (sunscreens, anti-oxidants (e.g., vitamins such as ascorbic acid, vitamin B, biotin, pantothenic acid, vitamin D, vitamin E and vitamin C), sodium bisulfite, yeast extract, gingko biloba, bisabolol, panthenol, alpha hydroxy acids, and oligosaccharides (e.g., melibiose)), chemotherapeutic and/or chemopreventative agents (e.g., placitaxel, cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives), steroids, anti-inflammatory agents (e.g., steroidal (e.g., corticosteroids (e.g., hydrocortisone), hydroxyltriamcinolone, alpha-methyl dexamethasone, dexamethasone-phosphate, beclomethasone dipropionate, clobetasol valerate, desonide, desoxycorticosterone acetate, dexamethoasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone) and non-steroidal anti-inflammatory agents (e.g., salicylates, acetic acid derivatives, fenamates, propionic acid derivatives and pyrazoles)), pigment modulating agents (e.g., depigmenting agents such as lipoic acid, arbutim, dihydrolipoic acid, resveratrol, ascorbic acid, kojic acid, hydroquinone, isoflavones, retinoids (e.g., retinol, retinoic acid, and retinyl palmitate), tyrosinase inhibitors, melanosome transfer inhibitors, selective cytotoxic agents for melanocytes, and natural extracts (e.g., licorice extract, gatuline A (pilewort extract), and micromerol (butylene glycol and apple extract))), exfoliating agents (e.g., organic hydroxy acids (e.g., alpha and beta hydroxy acids), salicylic acid, glycolic acid, lactic acid, 5-octanoyl salicylic acid, hydroxyoctanoic acid, hydroxycaprylic acid, lanolin fatty acids, sulphydryl compounds, protease or peptase enzymes (natural and bio-engineered), mimetic compounds that mimic hydroxyl acids, and bioactive metals (e.g., manganese, tin, and copper), and natural soy-based products), lipid molecules (e.g., sphingosine-1-phosphate and lysophosphatidic acid), amino acids (e.g., arginine and lysine), vitamin A, vitamin D, bradykinins, substance P, calcium gene-related peptide (CGRP), insulin, vascular endothelial growth factor (VEGF), thrombin, antibodies to platelet endothelial cells surface marker, compounds specifically binding adhesion molecules (e.g., ICAMs, NCAMs, PECAMs), extra-cellular matrix proteins (e.g., glycosaminoglycans), fibrous proteins (e.g., collagen; elastin, fibronectins, and laminin), growth factors (e.g., platelet derived growth factors (PDGF), epidertnal growth factor (EGF), keratinocyte growth factor (KGF), vascular endothelial growth factors (VEGFs), fibroblast growth factors (FGFs), transforming growth factors (TGFs), and insulin-like growth factor-1 (IGF-1)) tumor necrosis factor-alpha (TNF-alpha), tumor necrosis factor-beta (TNF-beta), and thymosin B4), anti-irritation agents (e.g., methyl nicotinate, corticosteroids, ascorbic acid, and acetic acid), anti-cellulite agents (e.g., xanthine compounds such as caffeine, theophylline, theobromine, and aminophylline), anti-fungal agents (e.g., terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide), anti-bacterial agents (e.g., antibiotics, penicillins, cephalosporins, carbacephems, cephamycins, carbapenems, monobactams, aminoglycosides, glycopeptides, quinolones, tetracyclines, macrolides, fluoroquinolones, and derivatives thereof), moisturizing agents (e.g., polyhydric alcohols (e.g., glycerin, propylene glycol, 1,3-buthyleneglycol, polyethylene glycol, sorbitol, isoprene glycol, and POB methyl glucoside), saccharides (e.g., trehalose, pullulan, and maltose), and biological polymers (e.g., sodium hyaluronate, chondroitin sodium sulfate, collagen, elastin, amino acids, sodium lactate, pyrrolidone sodium carboxylate, and urea), emollients (e.g., lanolin, spermaceti, mineral oil, paraffin, petrolatum, white ointment, white petroleum, yellow ointment, vegetable oils, waxes, cetyl alcohol, glycerin, hydrophilic petrolatum, isopropyl myristate, myristyl alcohol, and oleyl alcohol), antioxidants (e.g., water-soluble antioxidants (e.g., sulfhydryl compounds, sulfhydryl derivatives (e.g., sodium metabisulfite and N-acetyl-cysteine), lipoic acid, dihydrolipoic acid, resveratrol, acetyl-cysteine (iniferine), lactoferrin, ascorbic acid, and ascorbic acid derivatives (e.g., ascorbyl palmitate and ascorbyl polypeptide)), oil-soluble antioxidants (butylated hydroxytoluene, retinoids (e.g., retinol and retinyl palmitate), tocopherols (e.g., tocopherol acetate), tocotrienols, and ubiquinone), and natural extracts (e.g., extracts containing resveratrol, flavonoids and isoflavonoids and derivatives thereof (e.g., genistein and diadzein) such as grape seed, green tea, pine bark, propolis, and legume extracts), anti-swelling agents (e.g., lanolin, aloe vera extract, hydrocortisone, and menthol), anesthetics (e.g., ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobutyl p-aminobenzoate, ketamine, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocalne, procaine, propanocaine, proparacaine, propipocaine, propoxycaine, pseudococaine, pyrrocaine, ropivacaine, salicyl alcohol, tetracaine, tolycaine, trimecaine, zolamine, and pharmaceutically acceptable salts thereof), anti-viral agents (e.g., amantadine hydrochloride, rimantadin, acyclovir, famciclovir, foscarnet, ganciclovir sodium, idoxuridine, ribavirin, sorivudine, trifluridine, valacyclovir, vidarabin, didanosine, stavudine, zalcitabine, zidovudine, interferon alpha, and edoxudine), nutrients (e.g., vitamins (e.g., vitamin A, vitamin B, vitamin C, and vitamin E), essential amino acids, and essential fatty acids), cosmetic agents, coloring agents, and fragrances.

Protocols and procedures which facilitate formulation of the topical compositions of the invention can be found, for example, in Cosmetic Bench Reference, Cosmetics & Toiletries, Allured Publishing Corporation, Illinois, 2005 and in International Cosmetic Ingredient Dictionary and Handbook. 10th ed. Edited by Gottschalck and McEwen. Washington, Cosmetic, Toiletry and Fragrance Association, 2004.

The compositions comprising the particles of the instant invention may be conveniently formulated for administration with any pharmaceutically/cosmetically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the particles in the chosen medium may be varied and the medium may be chosen based on the desired route of administration of the pharmaceutical preparation. Except insofar as any conventional media or agent is incompatible with the nanoparticles to be administered, its use in the pharmaceutical preparation is contemplated.

The dose and dosage regimen of particles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the particle's biological activity. The dosage ranges for the administration of the compositions of the invention are those large enough to produce the desired effect (e.g., curing, relieving, treating, and/or preventing the disease or disorder, the symptoms of it, or the predisposition towards it). The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

Selection of a suitable pharmaceutical preparation will also depend upon the mode of administration chosen. For example, the particles of the invention may be administered by direct injection or intravenously. In this instance, a pharmaceutical preparation comprises the nanoparticle dispersed in a medium that is compatible with the site of injection.

Particles of the instant invention may be administered by any method. For example, the particles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the nanoparticles are administered topically, intravenously or intraperitoneally. Pharmaceutical preparations for injection are known in the art. If injection is selected as a method for administering the particle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a particle of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical preparations may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical preparation comprising the nanoparticles may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a composition comprising a nanoparticle of the instant invention and, particularly, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the compositions of the instant invention.

The instant also encompasses delivering the nanoparticle of the instant invention to a cell in vitro (e.g., in culture). The nanoparticle may be delivered to the cell in at least one carrier.

III. Definitions

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of an oxidative stress related disease or disorder results in at least a reduction in the amount of (the scavenging of) reactive oxygen species (ROS).

A "therapeutically effective amount" of a compound or a pharmaceutical composition refers to an amount effective to prevent, inhibit, treat, or lessen the symptoms of a particular disorder or disease.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

As used herein, the term "antioxidant" refers to compounds that neutralize the activity of reactive oxygen species or inhibit the cellular damage done by the reactive species or their reactive byproducts or metabolites. The term "antioxidant" may also refer to compounds that inhibit, prevent, reduce or ameliorate oxidative reactions. Examples of antioxidants include, without limitation, vitamin E, vitamin C, ascorbyl palmitate, vitamin A, carotenoids, beta carotene, retinoids, xanthophylls, lutein, zeaxanthin, flavones, isoflavones, flavanones, flavonols, catechins, ginkgolides, anthocyanidins, proanthocyanidins, carnosol, carnosic acid, organosulfur compounds, allylcysteine, alliin, allicin, lipoic acid, omega-3 fatty acids, eicosapentaeneoic acid (EPA), docosahexaeneoic acid (DHA), tryptophan, arginine, isothiocyanates, quinones, ubiquinols, butylated hydroxytoluene (BHT), butylated hydroxyanisole (BHA), super-oxide dismutase mimetic (SODm), and coenzymes-Q.

The terms "reactive oxygen species," or "oxidative species," as used herein, refer to oxygen derivatives from oxygen metabolism or the transfer of electrons, resulting in the formation of "free radicals" (e.g., superoxides or hydroxyl radicals).

As used herein, the terms "host," "subject," and "patient" refer to any animal, including humans.

As used herein, the term "prevent" refers to the prophylactic treatment of a subject who is at risk of developing a condition (e.g., cancer) resulting in a decrease in the probability that the subject will develop the condition.

The following example provides illustrative methods of practicing the instant invention, and is not intended to limit the scope of the invention in any way.

EXAMPLE

Materials and Methods

Materials

Fullerene ($C_{60}$), PVP 10 kDa (K15), toluene, chloroform, hypoxanthine (HX), xanthine oxidase (XO), angiotensin II (Ang II), riboflavin 50-monophosphate sodium salt dehydrate (FMN) and superoxide dismutase (SOD1) were purchased from Sigma-Aldrich Co. (St. Louis, Mo.). Poly(2-ethyl-2-oxazoline) 5 kDa (PEtOx) was purchased from Polysciences Inc. (Warrington, Pa.). Poly(2-ethyl-2-oxazoline)-co-poly (2-butyl-2-oxazoline) 8 kDa (P($EtOx_{50}$-co-$BuOx_{20}$)) was synthesized and purified as described (Tong et al. (2010) Mol. Pharm., 7:984-92). Methoxycarbonyl-2,2,5,5-tetramethyl-pyrrolidine (CMH), deferoxamine methanesulfonate salt (DF) and diethyldithiocarbamic acid sodium (DETC) were from Noxygen Science Transfer & Diagnostics GmbH (Elzach, Germany). Fullerene monoclonal antibody (mouse IgG1) was purchased from Santa Cruz Biotechnology, Inc. (Santa Cruz, Calif.). Alexa Fluor® 488 goat anti-mouse IgG and MitoTracker® Red FM were from Invitrogen (Carlsbad, Calif.). Nunc Lab-Tek II chamber slide system was from Thermo Fisher Scientific (Waltham, Mass.). 25 nm colloidal gold-labeled anti-mouse IgG was from Aurion (Hatfield, Pa.).

Devices

A LAMBDA 25 UV-vis spectrometer (PerkinElmer, Waltham, Mass.) and a Nicolet 380 FT-IR spectrometer (Thermo Scientific, Waltham, Mass.) were used for the measurement of absorbance and infrared spectra of $C_{60}$-polymer complexes. Particle size and size distribution were determined by dynamic light scattering (DLS) using Nano series Zetasizer (Malvern Instruments Inc., Westborough, Mass.). Atomic force microscopy (AFM) was carried out with MFP-3D microscope (Asylum Research, Santa Barbara, Calif.) mounted on inverted optical microscope (Olympus, Center Valley, Pa.). Transmission electron microscopy (TEM) was done with Tecnai GZ Spirit TW device (FEI, Hillsboro, Oreg.) equipped with an AMT digital imaging system (Danvers, Mass.). Electron paramagnetic resonance (EPR) spectroscopy was performed with a Bruker Biospin e-scan spectrometer (Bruker, Billerica, Mass.). Confocal microscopy was carried out by LSM 510 Meta Confocal imaging system (Carl Zeiss, Peabody, Mass.).

Preparation of $C_{60}$-Polymer Complexes

The aqueous dispersions of $C_{60}$-polymer complexes were prepared by a thin film hydration method with minor modifications (Ungurenasu et al. (2000) J. Med. Chem., 43:3186-8; Xiao et al. (2006) Bioorg. Med. Chem. Lett., 16:1590-5). Briefly, 1 ml of fullerene in toluene (1 mg/ml) was mixed with 3 ml of PVP or POx in chloroform and stirred at room temperature (r.t.) for 2 hours. The $C_{60}$ to polymer molar ratios were varied from 1:0.5 to 1:4. The solvents were removed in vacuo at 60° C. to form the thin films. The $C_{60}$-polymer complexes were readily dispersed in 1 ml of deionized water ($DIH_2O$), in selected cases using 1-2 minute sonication. Excess of unincorporated fullerene was removed by centrifugation (10,000 rpm, 5 minutes) and filtration through a 0.45 μM filter resulting in a clear yellow colloidal solution. The complexes were dialyzed against water overnight to eliminate the residual toluene and excess of the polymer, and then lyophilized and stored at r.t. for further characterization.

Characterization of $C_{60}$-Polymer Complexes

UV-Vis Spectroscopy

UV-vis spectra of $C_{60}$-polymer complexes were recorded and used to determine the concentration of solubilized fullerene by absorbance at 340 nm (the molar absorptivity 49,000 cm l/mol (Yamakoshi et al. (1994) J. Chem. Soc. Chem. Commun., 4:517-8)). The fullerene loadings were expressed as % wt. of the dispersed phase ($C_{60}$-polymer complex dry powder weighted after lyophilization of the dispersions).

Infrared (IR) Spectroscopy

IR spectra were recorded using lyophilized powders of free polymers or $C_{60}$-polymer complexes.

Dynamic Light Scattering (DLS)

Effective hydrodynamic diameters of the particles were measured by photon correlation spectroscopy (i.e. dynamic light scattering, DLS) in a thermostatic cell at a scattering angle of 90° using the same instrument equipped with a Multi Angle Sizing Option (BI-MAS). Briefly, 0.5 ml of complexes dissolved in $DIH_2O$ at 100 μM $C_{60}$ was used for the measurement. All measurements were performed at 25° C. Software provided by the manufacturer was used to calculate the size of the particles and polydispersity indices. All the formulations were prepared and measured three times in a parallel manner. The data are presented as means±SEM. For the stability testing, 0.5 ml of complexes with different pH (pH 2-10), ionic strength (0-1 M NaCl), concentration (1-100 μM) and storage time (1 day-3 weeks at r.t.) were used.

AFM and TEM Imaging

For AFM imaging, 10 μl of $C_{60}$-polymer complexes were dropped on the positive APS mica. The sample was dried under vacuum for 1 hour and used for AFM scanning. The data are presented as means±SEM. For TEM imaging, 10 μl of $C_{60}$-polymer complexes were dropped at the top of carbon-coated grid. 1% of uranyl acetate solution was applied as the negative staining. The grid was dried for 3 minutes at r.t. and sent for TEM imaging.

EPR Spectroscopy

The ability of $C_{60}$-polymer complexes to scavenge superoxide was measured by EPR spectroscopy, as reported (Rosenbaugh et al. (2010) Biomaterials 31:5218-26). Briefly, superoxide generated by HX—XO or a photosensitizer, FMN, was detected using the CMH spin probe. Samples contained 0.025 mM DF and 0.005 mM DETC buffer (pH 7.4), 0.025 mM CMH, 0.025 mM HX and 10 mU XO (or 0.02 mM FMN instead of HX—XO) and $C_{60}$-polymer complexes at different concentrations. After complete mixing, each sample was incubated at r.t. for 5 minutes and 50 μl of the sample was loaded into a glass capillary, which was then inserted into the capillary holder of the EPR spectrometer. The CMH radical signal was recorded and EPR spectrum amplitude was quantified.

Cell Culture

CATH.a neuronal cells (ATCC CRL-11179™) were seeded in 6-well plates at 500,000 cells/well or in 24-well plates at 150,000 cells/well (for cytotoxicity studies only) in RPMI-1640 medium (Invitrogen, Carlsbad, Calif.) supplemented with 1% penicillin/streptomycin, 4% fetal bovine serum (Invitrogen, Carlsbad, Calif.) and 8% horse serum (Gibco, Life Tech., Grand Island, N.Y.). As previously described (Yin et al. (2010) Am. J. Physiol. Cell Physiol., 298:C857-65), CATH.a neurons were cultured at 37° C. with 95% humidity and 5% $CO_2$, and differentiated by adding 1 mM of fresh N-6,2'-O-dibutyryl adenosine 3',5'-cyclic-monophosphate (AMP, Sigma-Aldrich Co. St. Louis, Mo.) every 2 days. The cells were typically cultured for 6-8 days for full expression of Ang II receptors on the cell surface. Madin Darby Canine Kidney (MDCK) cells (ATCC, CCL-34), and human liver carcinoma Hep G2 cells (ATCC, HB-8065) were seeded in 96-well plates at 10,000 cells/well in DMEM medium (Invitrogen, Carlsbad, Calif.) supplemented with 1% penicillin/streptomycin and 10% fetal bovine serum. These cells were cultured at 37° C. with 95% humidity and 5% $CO_2$ for 48 hours.

Cytotoxicity Assay

Cytotoxicity of $C_{60}$-polymer complexes was determined using a cell counting kit (Dojindo Molecular Technologies, Inc., Gaithersburg, Md.) according to the protocol provided by the manufacturer. Briefly, cells were seeded in 96-well plates (MDCK, Hep G2) or 24-well plates (CATH.a) and cultured as described above until the media was replaced with the fresh one containing different concentrations of $C_{60}$ complexes. After that the cells were incubated with the complexes for additional 24 hours. The media was then changed for the fresh media containing 10% CCK-8 solution (2-(2-methoxy-4-nitrophenyl)-3-(4-nitrophenyl)-5-(2, 4-disulfophenyl)-2H-tetrazolium, monosodium salt). The absorbance at 450 nm was recorded in a plate reader (Molecular Devices, Sunnyvale, Calif.) after 1 hour incubation. The cell viability was calculated as follows: Cell Viability (%)=$(A_{sample}-A_{blank})(A_{control}\times A_{blank})\times 100\%$. Each treatment was repeated three times and data are presented as means±SEM.

Cellular Uptake in CATH.a Neuronal Cells

After 6-8 days culture, in 6-well plates CATH.a neuronal cells were exposed to 100 μM of $C_{60}$-polymer complexes in fresh full medium for 24 hours. Then cells were washed twice with 1.0 ml of 0.1M phosphate buffer (pH 7.4) and lysed with 0.5 ml of 1% triton X-100. The UV-vis spectra of cell lysate supernatant were recorded by a spectrometer. The absorbance was normalized by the cellular protein concentration determined by MicroBCA assay (Pierce, Rockford, Ill.). The spectrum of the control group (without treatment) was subtracted.

Immunofluorescence Staining and Confocal Microscopy

The immunofluorescence staining of fullerene has been described (Kato et al. (2010) J. Photochem. Photobiol. B., 98:144-51; Chirico et al. (2007) Exp. Dermatol., 16:429-36). After 6-8 days culture, CATH.a neuronal cells in chamber slides were incubated with 100 μM $C_{60}$-polymer complexes in fresh full medium for 24 hours. Cells were washed twice with 1.0 ml of 0.1 M phosphate buffer (pH 7.4), stained with MitoTracker® Red FM for 30 minutes and then fixed with 4% paraformadehyde for 30 minutes at r.t. After brief blocking, the fixed cells were incubated with fullerene antibody (1:30 dilution) overnight at 4° C. and then secondary antibody labeled with Alexa Fluor® 488 (1:200 dilution) for 2 hours at r.t. The slides were sealed with coverslips and images were collected using confocal microscopy.

Immunogold Labeling and TEM Imaging

The immunogold labeling of fullerene has been described (Chirico et al. (2007) Exp. Dermatol., 16:429-36). Briefly, CATH.a neuronal cells were exposed to 100 μM of $C_{60}$-PEtOx complex and cultured as described above. They were then washed twice with 0.1M phosphate buffer and fixed with 2.5% glutaraldehyde in 0.2 M cacodylate at r.t. for 20 minutes. Then cells were postfixed in 1% osmium tetroxide in 0.2 M cacodylate for 1 hour, dehydrated in ethanol solution and embedded in Agar 100 resin. Thin sections were prepared and incubated with fullerene antibody (1:30 dilution) for 1 hour at r.t. and then incubated with 25 nm colloid gold-labeled secondary antibody (1:10 dilution) for 1 hour at r.t. The sections were stained with 1% uranyl acetate and the images were collected using a TEM.

Intracellular EPR Spectroscopy

EPR spectroscopy was used to measure the intracellular superoxide levels in CATH.a neuronal cells as described (Rosenbaugh et al. (2010) Biomaterials 31:5218-26). After 6-8 days culture, CATH.a neuronal cells in 24-well plates were incubated with $C_{60}$-polymer complexes at different concentrations in fresh full medium for 24 hours. Then, cells were washed twice with 0.5 ml of EPR buffer (pH 7.4), and incubated with 1 ml of EPR buffer containing 200 μM of CMH as the intracellular spin probe for 1 hour at 37° C. After incubation ca. 0.9 ml of buffer was aspirated from the well, the cells were scraped from the well and re-suspended with the remaining buffer, and 100 ml of this cell suspension was stimulated with 1 ml of Ang II (100 nM) to generate intracellular superoxide. Immediately after full mixing, 50 μl of cell suspension were loaded into the EPR spectrometer and the generation of superoxide over 10 minutes was recorded. The difference in EPR amplitude between the 1st scan (0 minute) and 10th scan (10 minutes) was interpreted as the Ang II-stimulated, superoxide-dependent signal. To control for the difference in cell number between samples, 10 μl of cell suspension were used for cell counting, and the EPR amplitude of each sample was normalized by cell number. Each treatment was repeated three times and data are presented as means±SEM.

Statistical Analysis

Statistical analysis was done using one-way ANOVA (LSD multiple comparisons). A minimum p-value of 0.05 was estimated as the significance level.

Results

Characterization of C60-Polymer Complexes

One type of $C_{60}$-PVP complex (based on PVP 10 kDa) and two types of $C_{60}$-POx complexes (based on a homopolymer, PEtOx 5 kDa, and a random copolymer, P(EtOx-co-BuOx) 8 kDa) were prepared. The chemical structures of these polymers and the proposed charge-transfer complex formation between fullerene and POx are shown in FIG. 1. The aqueous dispersions of these complexes were optically transparent and revealed the presence of fullerene in the UV-vis spectra (FIG. 2). For both $C_{60}$-PVP and $C_{60}$-POx complexes, similar spectra and specific absorbance of fullerene around 340 nm were recorded. The net amount of solubilized fullerene increased for both $C_{60}$-PVP and $C_{60}$-P(EtOx-co-BuOx) mixtures as the $C_{60}$: polymer molar ratio increased from 1:0.5 to 1:4. However, the loading of fullerene practically did not change and varied from 0.6% to about 1% wt. of dispersed phase. Generally, the maximal loading was observed at 1:1 ratio of the components in the initial mixture (Table 1). Interestingly, the solubilization capacity of the more hydrophobic of the two POx, P(EtOx-co-BuOx), was comparable to PVP having similar molecular weight, while a more hydrophilic POx, PEtOx, incorporated less fullerene than PVP. Furthermore, the most hydrophilic POx, poly(2-methyl-2-oxazoline) (PMeOx), 5 kDa, was incapable of forming stable dispersions with fullerene. These results clearly indicate that the hydrophobicity of POx significantly affects their solubilization capacity for fullerene.

TABLE 1

Characterization of $C_{60}$-polymer complexes.

| Formulations | Particle size (nm)[a] | Polydispersity index (PDI) | Maximal fullerene loading[d] (w/w %) |
|---|---|---|---|
| $C_{60}$-PVP 40 kd | 220 | 0.15-0.20 | 0.8 |
| $C_{60}$-PVP 10 kd | 94.9 ± 15.21[b] | 0.227 ± 0.024 | 1.0 |
| $C_{60}$-PEtOx 5 kd | 156.5 ± 22.48[c] | 0.217 ± 0.022 | 0.5 |
| $C_{60}$-P(EtOx-co-BuOx) 8 kd | 132.6 ± 5.94[c] | 0.195 ± 0.019 | 1.0 |

[a]Particle size and size distribution do not change upon dilution (1-100 μM $C_{60}$), alteration of pH (pH 2-10) or ionic strength (0-1M NaCl) of the final dispersion.
[b]Aggregation is observed after 2 weeks at r.t.
[c]For POx, no aggregation is observed upon storage at r.t. for 3 weeks.
[d]Weight percent of fullerene in dispersion per dispersed phase.

The charge-transfer interaction between PVP and pristine fullerene has been studied (Ungurenasu et al. (2000) J. Med. Chem., 43:3186-8). As shown in FIG. 2, an absorption band at about 430 nm is attributed to the formation of $C_{60}$-PVP charge-transfer complex. This absorption band was also observed at 430 nm for $C_{60}$-POx complex (FIG. 2B). It has been reported that there is a red-shift for the carbonyl stretching mode of IR spectrum from 1669 $cm^{-1}$ for the free PVP to 1662 $cm^{-1}$ for the complex (Yu-Huei et al. (1999) Fullerene Sci. Techn., 7:807-23). This shift indicates that the amide groups of PVP are involved in the charge-transfer interaction between the polymer and fullerene. In the present study, only a minor red-shift of 2 $cm^{-1}$ was found in the IR spectra of $C_{60}$-POx complex. In these cases the major peak corresponding to the stretching mode of the carbonyl group (amide I band) of PEtOx shifted from 1629 $cm^{-1}$ to 1627 $cm^{-1}$ (FIG. 2C).

The effective size and polydispersity indices (PDI) of the dispersed particles were measured by DLS (Table 1). The representative size distributions of $C_{60}$-PVP and $C_{60}$-POx particles are shown in FIG. 3. $C_{60}$-POx complexes formed larger particles (ca. 150 nm and 130 nm for $C_{60}$-PEtOx and $C_{50}$-P(EtOx-co-BuOx) respectively) compared to $C_{60}$-PVP complex (ca. 90 nm). For all the polymers used the PDI indices ranged from ca. 0.15 to 0.25. Notably, the particle size and size distribution did not change upon altering pH or ionic strength, and 100-times dilution of the initial dispersion. Furthermore, they did not aggregate upon storage at r.t. for at least 2 weeks. After this period, aggregation and increase in PDI (to PDI 0.4) was recorded for the $C_{60}$-PVP complex, while both $C_{60}$-POx complexes remained stable for an additional week. Despite such remarkable stability in an aqueous dispersion, the fullerene quantitatively recovered and separated from the polymers by extraction into toluene (3:1 v/v).

The representative AFM images are shown in FIG. 3. The AFM revealed generally spherical morphology of the particles. In the dry state these particles had mean diameters ranging from 40 nm ($C_{60}$-PVP) to 96 nm ($C_{60}$-PEtOx) and mean heights ranging from 5.6 nm ($C_{60}$-PVP) to 9.7 nm ($C_{60}$-PEtOx) (Table 2). The spherical morphology was further reinforced by TEM (FIG. 4), which also suggested that particles are rather heterogeneous, consistent with both DLS and AFM. TEM further revealed possible inner-structures within some of the $C_{60}$-PVP and $C_{60}$-POx particles exhibited as dense formations with relatively high electron density (the dark regions marked by arrows in FIG. 4). This may indicate that these complexes are composed of one (or more) fullerene-rich domain(s) and a hydrated polymer-rich domain.

TABLE 2

AFM characterization of $C_{60}$-polymer complexes.

| Formulations | Mean diameter (nm)[a] | Mean height (nm) | mean volume ($nm^3$) |
|---|---|---|---|
| $C_{60}$-PVP | 40.1 ± 1.38 | 5.6 ± 0.1 | 9640 ± 356 |
| $C_{60}$-PEtOx | 96.0 ± 3.04 | 9.7 ± 0.5 | 49,900 ± 3990 |
| $C_{60}$-P(EtOx-co-BuOx) | 57.7 ± 2.77 | 6.1 ± 0.3 | 28,800 ± 5750 |

Superoxide Scavenging of $C_{60}$-Polymer Complexes

The radical scavenging capabilities of antioxidants can be quantitatively evaluated by EPR spectroscopy. In this experiment, superoxide was generated using two different sources: (1) an HX+XO catalytic system or (2) a photosensitizer, FMN. Dose-dependent superoxide scavenging was found in all the formulations tested and was independent of the superoxide source (FIGS. 5A and 5B). The representative EPR spectra are also shown in FIGS. 5C-5G. Treatment with SOD1, which specifically scavenges superoxide, completely abolished the EPR spectrum (FIG. 5G); thus, corroborating the fidelity of the assay and showing that the CMH radical detected by EPR spectroscopy is superoxide dependent. The $C_{60}$-PVP and $C_{60}$-PEtOx complexes exhibited comparable superoxide scavenging activity while $C_{60}$-P(EtOx-co-BuOx) was the least effective. The same scavenging effects as shown for $C_{60}$-polymer complexes were not observed in the presence of the same concentrations of polymers alone.

Cytotoxicity

The possible toxicity of carbon nanomaterials has been a concern for their biological applications (Nel et al. (2006) Science 311:622-7; Mori et al. (2006) Toxicology 225:48-54; Sayes et al. (2004) Nano Lett., 4:1881-7). However, it has been reported that surface functionalization and formulation can efficiently attenuate the toxicity of "naked" fullerene and other carbon nanomaterials such as carbon nanotubes (Sayes et al. (2004) Nano Lett., 4:1881-7; Sayes et al. (2006) Toxicol. Lett., 161:135-42). Therefore cytotoxicity of $C_{60}$-polymer complexes was comprehensively evaluated using three different cell models: MDCK, Hep G2 and CATH.a neuronal cells (FIG. 6). No cytotoxicity was observed upon incubation of MDCK cells with either $C_{60}$-PVP or $C_{60}$-P(EtOx-co-BuOx) complexes for 24 hours (FIG. 6A). However, a minor inhibition of cell growth (80% cell viability) was found in the $C_{60}$-PEtOx treatment groups at the highest concentration, 100 μM of $C_{60}$. In Hep G2 cells, $C_{60}$-PVP and $C_{60}$-PEtOx exhibited similar toxicity profiles with some toxicity (80% cell viability) at 100 μM of $C_{60}$ (FIG. 6B). Likewise, $C_{60}$-PVP and $C_{60}$-PEtOx were not toxic to CATH.a cells up to 50 μM, but decreased cell viability to 80% at 100 μM and were considerably toxic (30% cell viability, $p<0.01$) at 200 μM (FIG. 6C). Based on these results, $C_{60}$-PVP and $C_{60}$-PEtOx complexes were selected for further investigations in the neuron models and the 100 μM was set as the highest concentration in these studies.

Neuronal Cell Uptake and Distribution

Cellular uptake of $C_{60}$-PVP and $C_{60}$-PEtOx into CATH.a neuronal cells was observed, as determined by the UV-vis spectra of cell lysates (FIG. 7A). As shown in FIG. 7A, after 24 hours of incubation the lysates displayed specific absorption of fullerene in the vicinity of 340 nm. Absorption of fullerene in neurons incubated with C60-PEtOx was considerably greater than that of $C_{60}$-PVP, which suggests that POx-based formulation enhances binding and/or uptake of $C_{60}$ in neuronal cells. The intracellular localization of $C_{60}$ was further examined by immunofluorescence and immunogold labeling (FIGS. 7B and 7C). Consistent with the UV-vis analysis, CATH.a neuronal cells treated with $C_{60}$-PEtOx exhibited much greater uptake of $C_{60}$, than the $C_{60}$-PVP-treated neurons (FIG. 7B). No obvious co-localization of fullerene and Mitotracker® Red was observed, suggesting that fullerene did not accumulate in the mitochondria after internalization into the cells. The immunogold labeling showed that fullerene was mainly distributed in the cytoplasm and nuclear region (FIG. 7C). No fullerene was found in the mitochondria using this method.

Intracellular Superoxide Scavenging

EPR spectroscopy was used to measure intracellular levels of superoxide in Ang II-stimulated CATH.a neuronal cells. As shown in FIG. 8, a significant increase in EPR amplitude, indicating an increase in intracellular superoxide, was detected after 10 minutes of Ang II stimulation (control vs. control p Ang II, $p<0.01$). Significant superoxide scavenging was observed upon exposure of cells to $C_{60}$-PEtOx complex at 100 μM ($p<0.01$) and 50 μM ($p<0.05$). Dose-dependent scavenging of intracellular superoxide was clearly evident in this case. Furthermore, 100 μM $C_{60}$-PEtOx significantly reduced intracellular superoxide levels in CATH.a neuronal cells incubated with another superoxide generator, menadione (FIG. 8A). In contrast to $C_{60}$-PEtOx, $C_{60}$-PVP did not decrease levels of intracellular superoxide (FIG. 8B), which may be due to the limited cellular uptake of this formulation (FIG. 7).

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising at least one fullerene and at least one oxazoline polymer, wherein said fullerene is complexed with said oxazoline polymer, wherein said oxazoline polymer is a poly(2-alkyl-2-oxazoline), and wherein the composition comprises at least one pharmaceutically acceptable carrier or cosmetically acceptable carrier.

2. The composition of claim 1, wherein said fullerene is pristine.

3. The composition of claim 1, wherein the fullerene is $C_{60}$.

4. The composition of claim 1, wherein said oxazoline polymer is a homopolymer.

5. The composition of claim 1, wherein said oxazoline polymer is a random or block copolymer.

6. The composition of claim 1, wherein said oxazoline polymer comprises 2-ethyl-2-oxazoline.

7. The composition of claim 6, wherein said oxazoline polymer is a homopolymer of 2-ethyl-2-oxazoline.

8. The composition of claim 6, wherein said oxazoline polymer is a copolymer comprising 2-ethyl-2-oxazoline.

9. The composition of claim 1, wherein the complexes comprise about 0.1% to about 5% fullerene.

10. The composition of claim 1 further comprising a cosmetically acceptable agent selected from the group consisting of sunscreens, anti-aging agents, chemotherapeutic agents, steroids, anti-inflammatory agents, exfoliating agents, lipid molecules, amino acids, vitamins, anti-irritation agents, anti-cellulite agents, anti-fungal agents, anti-bacterial agents, moisturizing agents, saccharides, emollients, antioxidants, anti-swelling agents, anesthetics, anti-viral agents, cosmetic agents, coloring agents, and fragrances.

11. A method for treating or inhibiting an oxidative stress associated disease or disorder in a subject in need thereof, said method comprising administering to said subject at least one composition of claim 1.

12. The method of claim 11, wherein said oxidative stress associated disease or disorder is selected from the group consisting of hypertension, heart failure, arthritis, cancer, neurodegenerative disorders, and cardiovascular diseases.

13. The method of claim 12, wherein said neurodegenerative disease is selected from the group consisting of Alzheimer's disease, Huntington's disease, Parkinson's disease, Lewy Body disease, amyotrophic lateral sclerosis, and prion disease.

14. The composition of claim 1, wherein said fullerene and said oxazoline polymer form a charge-transfer complex.

15. The composition of claim 1, wherein said complex of fullerene and the oxazoline polymer is a nanoparticle.

16. The composition of claim 1, wherein said complex of fullerene and the oxazoline polymer has an average diameter of about 50 nm to about 500 nm.

17. The composition of claim 1, wherein said complex of fullerene and the oxazoline polymer has an average diameter of about 100 nm to about 200 nm.

* * * * *